(12) United States Patent
Iwasaki et al.

(10) Patent No.: US 6,458,948 B1
(45) Date of Patent: Oct. 1, 2002

(54) PROCESS FOR PRODUCING CARBOXYLIC ACID DERIVATIVE AND CONDENSING AGENT COMPRISING QUATERNARY AMMONIUM SALT

(75) Inventors: Fumiaki Iwasaki, Tokuyama; Shohei Tani, Kobe; Munetaka Kunishima, Kobe; Keiji Terao, Kobe; Michiko Miharu, Tokuyama; Naoki Hirano, Tokuyama; Masako Saijyo, Tokuyama, all of (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 09/674,930

(22) PCT Filed: Feb. 15, 2000

(86) PCT No.: PCT/JP00/00834

§ 371 (c)(1),
(2), (4) Date: Dec. 11, 2000

(87) PCT Pub. No.: WO00/53544

PCT Pub. Date: Sep. 14, 2000

(30) Foreign Application Priority Data

Mar. 8, 1999 (JP) .......................................... 11-060765
May 18, 1999 (JP) .......................................... 11-137693
Oct. 15, 1999 (JP) .......................................... 11-293202

(51) Int. Cl.$^7$ ..................... C07D 251/46; C07D 501/18
(52) U.S. Cl. ..................... 540/219; 544/219; 546/133; 548/190; 560/1; 560/8; 560/9; 560/12; 564/123; 564/138; 564/139

(58) Field of Search .......................... 544/219; 540/219

(56) References Cited

U.S. PATENT DOCUMENTS 3,826,788 A * 7/1974 Froehlich et al. .......... 260/91.3
3,966,680 A * 6/1976 Wear et al. .................... 260/47

FOREIGN PATENT DOCUMENTS

EP          41082    * 7/1975
JP     50 82087    * 7/1975

OTHER PUBLICATIONS

Kaminski et al., J. Org. Chem. 63(13) 4248–4255, 1998.*
Saigo et al., Bull. Chem. Soc. Jpn., 50(7), 1863–1866, 1977.*
Kaminski, Tetrahedron Letters, 26(24) 2901–2904, 1985.*

* cited by examiner

Primary Examiner—Mukund J. Shah
Assistant Examiner—Venkataraman Balasubramanian
(74) Attorney, Agent, or Firm—Sherman & Shalloway

(57) ABSTRACT

A method of preparing carboxylic acid derivatives comprising mixing a quaternary ammonium salt having a particular triazine ring in the molecules thereof, a carboxylic acid compound and a compound having a nucleophilic functional group, to condense the carboxylic acid with the compound having the nucleophilic functional group. The invention further provides a condensing agent comprising the quaternary ammonium salt. The condensation is conducted under mild conditions to form carboxylic acid derivatives and, particularly, amide compounds or ester compounds maintaining high yields.

10 Claims, No Drawings

PROCESS FOR PRODUCING CARBOXYLIC ACID DERIVATIVE AND CONDENSING AGENT COMPRISING QUATERNARY AMMONIUM SALT

TECHNICAL FIELD

The present invention relates to a method of preparing carboxylic acid derivatives and, particularly, amide compounds or ester compounds.

The invention further relates to a condensing agent comprising a quaternary ammonium salt and, particularly, to a condensing agent that is preferably used for the preparation of amide compounds or ester compounds.

BACKGROUND ART

Carboxylic acid derivatives and, particularly, amide compounds and ester compounds are very important compounds for forming basic skeleton of various organic compounds such as medicine, agricultural chemicals, dyestuffs, high-molecular compounds, etc. Therefore, study has long been forward concerning how to prepare carboxylic acid derivatives.

As methods of preparing amide compounds, for example, there have generally been proposed a method of preparing amide compounds by the exchange reaction of ester compounds with amine compounds, as well as a method of preparing amide compounds directly from carboxylic acid compounds and amine compounds. As methods of preparing ester compounds, there have been generally proposed a method of preparing ester compounds directly from carboxylic acid compounds and alcohol compounds in the presence of an acid, and a method of preparing ester compounds by forming a carboxylic acid halide by reacting carboxylic acid compounds with an acid halide agent such as thionyl chloride, and acting it upon an alcohol compound.

However, the method of preparing amide compounds is conducted under a heated condition, and cannot be applied to the compounds that are thermally unstable or to the compounds having an amino group and an alkoxycarbonyl group in the same molecule. Further, the method of preparing ester compounds is conducted under an acidic condition, and cannot be applied to compounds that are not stable against acids.

In order to solve this problem, a variety of methods have been proposed by using a condensing agent for preparing amide compounds under mild conditions. A method that is most widely used industrially is the one that uses carbodiimide condensing agents as represented by a dicylohexyl-carbodiimide and a 1-ethyl-3-(3-dimethylaminopropyl) carbodiimide hydrochloride.

However, many of the carbodiimide condensing agents are those compounds that cause such problems as a rash, and require careful attention from the standpoint of working environment. Besides, when they are used for the condensation reaction in protonic organic solvent, a high reaction yield is not expected.

While the carbodiimide condensing agents cause rash to the skin and require attention for the handling thereof, a 4-(4,6-dimethoxy-1,3,5-triazin-2-yl)-4-methylmorpholinium chloride proposed as a condensing agent for the synthesis of amide compounds by Z. J. Kaminski et al. [Journal of Organic Chemistry, Vol. 63, pp. 4248–4255, 1998] is free from the above-mentioned problem and is drawing attention.

As a method of preparing ester compounds under mild conditions, further, a method has been proposed by Mukaiyama et al. that uses a condensing agent comprising a pyridinium oxide compound (Bulletin of Chemical Society of Japan, Vol. 50, pp. 1863–1866, 1977).

According to the method of preparing amide compounds by using a condensing agent proposed by Kaminski et al disclosed in the above literature, however, the carboxylic acid compound and the condensing agent are reacted together in an equal molar amount to once form a reactive derivative which is an intermediate product and, then, the reactive derivative is reacted with the amine compounds to obtain an amide compound. Therefore, the yield greatly fluctuates ranging from 17 to 73%, which is not satisfactory.

Further, the pyridinium oxide compound used for the preparation of the ester compounds must use methyl iodide that has been pointed out to be carcinogenic at the time of preparing the pyridinium oxide compound, and, hence, requires careful attention concerning the working environment.

Thus, preparations of the carboxylic acid derivatives using the conventional condensing agents are never satisfactory with regard to reaction yield, handling of the condensing agent, or safety during the preparation thereof.

DISCLOSURE OF THE INVENTION

It is an object of the present invention to provide a method of preparing carboxylic acid derivatives, which is capable of conducting the condensation reaction under mild conditions and of obtaining carboxylic acid derivatives and, particularly, amide compounds or ester compounds in high yields.

It is another object of the present invention to provide a condensing agent that makes it possible to obtain carboxylic acid derivatives in high yields.

According to the present invention, there is provided a method of preparing carboxylic acid derivatives comprising mixing a quaternary ammonium salt represented by the following general formula (I), a carboxylic acid compound and a compound having a nucleophilic functional group, to condense the carboxylic acid with the compound having the nucleophilic functional group, $$\left[ {}^{n+}E \underset{aZ^{-\frac{n}{a}}}{\left( \begin{array}{c} \diagup OR_1 \\ N \diagdown \\ \diagdown N \diagup \\ \diagdown OR_2 \end{array} \right)_n} \right] \quad (I)$$

wherein

E is a monovalent or divalent organic group having one or two tertiary amino groups;

n is 1 when E has one tertiary amino group, and is 2 when E has two tertiary amino groups, R1 and R2 are, independently from each other, alkyl groups having 1 to 4 carbon atoms or aryl groups having 6 to 8 carbon atoms;

a is 1 or 2, and is 1 when n is 1; and $Z^{-(n/a)}$ is a counter anion having a valency of (n/a), In the above general formula (I), E can be concretely expressed as

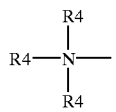

wherein R4 may be the same or different, and are monovalent organic groups in which at least an atom bonded to a quaternary nitrogen atom is a carbon atom, and plural R4 may be bonded together to form a divalent or trivalent organic group, when it has one tertiary amino group, and can be expressed as

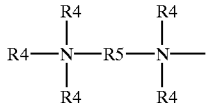

wherein R4 may be the same or different, and are monovalent organic groups in which at least an atom bonded to a quaternary nitrogen atom is a carbon atom, R5 is a divalent organic group in which at least an atom bonded to the quaternary nitrogen atom is a carbon atom, and all of, or some of, R4 and R5 may be bonded together to form one or more organic groups having valencies of 2 to 6, when it has two tertiary amino groups.

According to the preparation method of the present invention, the condensation is carried out in water, in a protonic organic solvent or in an organic solvent containing water and, particularly, by reusing the organic solvent containing water.

The compound having a nucleophilic functional group is an amine compound, and the carboxylic acid derivative is an amide compound. For example, (1) a cephem compound is prepared as an amide compound by using a 2-aminothiazolylacetic acid derivative as a carboxylic acid compound and by using a 7-aminocephalosporanic acid derivative as an amine compound. Further, (2) a peptide compound is prepared as an amide compound by using an aminoacid derivative of which the amino group is protected as a carboxylic acid compound and by using an aminoacid derivative of which the carboxylic acid is protected as an amine compound.

The compound having a nucleophilic functional group is an alcohol compound, and the carboxylic acid derivative is an ester compound. In this case, there is used an aminoacid compound derivative of which the amino group is protected as a carboxylic acid compound.

The quaternary ammonium salt represented by the above-mentioned general formula (I) is at least a quaternary ammonium salt selected from quaternary ammonium salts represented by the following general formulas (I') and (II),

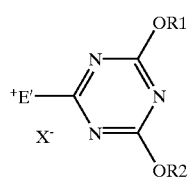

wherein
R1 and R2 are, independently from each other, alkyl groups having 1 to 4 carbon atoms or aryl groups having 6 to 8 carbon atoms;

E' is a monovalent organic group having one tertiary amino group; and

X- is a chloro anion, a perchlorate anion, or a boron tetrafluoride anion, and

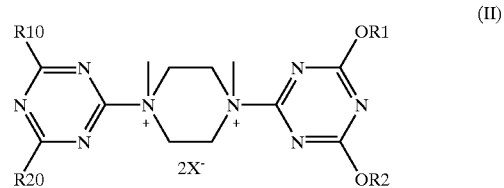

wherein R1 and R2 are, independently from each other, alkyl groups having 1 to 4 carbon atoms or aryl groups having 6 to 8 carbon atoms; and X- is a chloro anion, a perchlorate anion, or a boron tetrafluoride anion.

In this case, it is desired that the quaternary ammonium salt represented by the above general formula (I) is a quaternary ammonium salt represented by the following general formula (III),

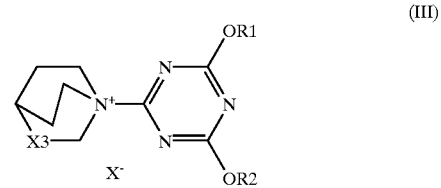

wherein R1 and R2 are, independently from each other, alkyl groups having 1 to 4 carbon atoms or aryl groups having 6 to 8 carbon atoms; and a group represented by —R3— is any one of the following groups,

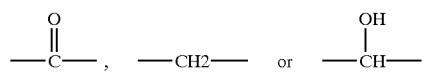

and,

X- is a chloro anion, a perchlorate anion or a boron tetrafluoride anion.

According to the present invention, there is further provided a novel quaternary ammonium salt represented by the above general formula (III).

According to the present invention, further, there is provided a condensing agent comprising a quaternary ammonium salt represented by the above general formula (I), particularly, a condensing agent comprising at least one quaternary ammonium salt selected from the quaternary ammonium salts represented by the above general formulas (I') and(II) and, particularly, a condensing agent comprising a quaternary ammonium salt represented by the above general formula (III).

According to the present invention, there is provided the use of the quaternary ammonium salt represented by the above general formula (I) as a condensing agent.

The preparation method of the present invention is different from the above-mentioned method of Kaminski et al. with respect to conducting the reaction in a state where a condensing agent, a carboxylic acid compound and an amine compound are existing together, and offers the reaction yield of as high as about 80%.

The 4-(4,6-dimethoxy-1,3,5-triazin-2-yl)-4-methyl morpholinium salt used in the above-mentioned method of Kaminski et al. is the one represented by the above-mentioned general formula (I') in which R1 and R2 are methyl groups, and E+ is a 4-methylmorpholinium cation. Among the condensing agents used in the preparation method of the invention, those other than the above were found this time, for the first time, as being useful as condensing agents.

According to the present invention, among the above-mentioned condensing agents, those in which the counter anion is a boron tetrafluoride anion are free from the problem of explosion, and favorably disperse in any organic solvent inclusive of water.

Further, starting materials of the condensing agents in which the counter anion is a chloro anion are easily available offering such an advantage as enabling the products to be cheaply produced.

BEST MODE FOR CARRYING OUT THE INVENTION

<Condensing Agent Comprising a Quaternary Ammonium salt>

The preparation method of the present invention uses a condensing agent comprising a quaternary ammonium salt represented by the above general formula (I).

As represented by the general formula (I), the condensing agent of the invention has a feature in that a molecule thereof has one or two chemical structures in which a triazine ring is bonded to a quaternary nitrogen atom. Another feature is that the triazine ring is a 1,3,5-triazine ring substituted by alkoxyl groups or aryloxyl groups at the fourth and sixth positions, and is bonded at the second position to the quaternary nitrogen atom.

The quaternary nitrogen atom has three other carbon atoms bonded thereto (two other carbon atoms bonded thereto when bonded to carbon atoms by double bond) in addition to the triazine ring. These carbon atoms may be included in three separate organic groups, or may be included in one or two organic groups. Since the tertiary amine is formed by nitrogen atom and three other carbon atoms, the condensing agent of the invention can be expressed by the tertiary amine and 4,6-alkoxyl or aryloxyl group-1,3,5-triazin-2-yl.

Preferred examples of the above general formula (I) include condensing agents comprising at least one quaternary ammonium salt selected from those quaternary ammonium salts represented by the above general formulas (I') and (II).

Among the quaternary ammonium salts represented by the above general formula (I'), the quaternary ammonium salt represented by the above general formula (III) is a compound prepared for the first time by the present inventors and preferably used as a condensing agent in the preparation method of the present invention.

In the above general formulas (I), (I'), (II) and (III), R1 and R2 are, independently from each other, alkyl groups having 1 to 4 carbon atoms or aryl groups having 6 to 8 carbon atoms. As the alkyl group having 1 to 4 carbon atoms, there can be exemplified methyl group, ethyl group, n-propyl group, isopropyl group and n-butyl group. As the aryl group having 6 to 8 carbon atoms, there can be exemplified phenyl group, tolyl group and xylyl group. Among them, an alkyl group such as methyl group or ethyl group and aryl group such as phenyl group can be preferably used from the standpoint of easy synthesis.

Further, E in the formula is a monovalent or divalent organic group having one or two tertiary amino groups, and is a tertiary amine or a tertiary diamine from such a standpoint that the tertiary amine is formed by the nitrogen atom and three other carbon atoms as described above.

As the tertiary amine or tertiary diamine, any tertiary amine or tertiary diamine available as industrial starting materials and reagents can be used without any limitation. Concrete examines of the tertiary amine or tertiary diamine include aliphatic tertiary amines or tertiary diamines such as N-methylmorpholine, N-ethylmorpholine, N-methylpyrrolidine, N-ethylpyrrolidine, N-methylpiperidine, N-ethylpiperidine, N-methylindoline, N-methylisoindoline, triethylamine, tributylamine, dimethylisopropylamine, dimethylcyclohexylamine, N,N,N',N'-tetramethylethylenediamine, N,N,N',N'-tetramethylpropanediamine, N,N,N',N'-tetramethylbutanediamine, 1,4-dimethylpiperadine and 1,4-diethylpiperadine; and aromatic tertiary amines or tertiary diamines such as pyridine, N,N-dimethylaniline, N,N-diethylaniline, N, N-dimethylbenzylamine, N, N-diethylbenzylamine, N-methylindole, N-methylisoindole, N-methylpyrrole, indolidine and N-methylcarbazole. Among them, there are preferably employed, from the standpoint of easy synthesis, aliphatic tertiary amines or tertiary diamines such as N-methylmorpholine, N-ethylmorpholine, N-methylpyrrolidine, N-ethylpyrrolidine, N-methylpiperidine, N-ethylpiperidine, triethylamine, tributylamine, dimethylisopropylamine, dimethylcyclohexylamine and 1,4-dimethylpiperadine; and aromatic tertiary amines such as pyridine, N,N-dimethylaniline, N,N-diethylaniline, N,N-dimethylbenzylamine, dimethylbenzylamine and N,N-diethylbenzylamine.

In the above general formula (I), $Z^{-(n/a)}$ is a counter anion having a valency of (n/a), i.e., having a valency of one or two, such as chloro anion, perchlorate anion, boron tetrafluoride anion, sulfuric acid anion or carbonic acid anion. In the above general formula (I), the number a is 2 when n is 2 and the counter anion has a valency of one. In this case, the two counter anions may be of different kinds.

In the present invention, among the quaternary ammonium salt represented by the above general formula (I), there are preferably used, from the standpoint of easy preparation, those in which R1 and R2 in any one of the formulas are methyl groups, ethyl groups, n-butyl groups or isopropyl groups, E is methylmorpholine, ethylmorpholine, methylpiperidine, ethylpiperidine, methylpyrrolidine, ethylpyrrolidine, dimethylcyclohexylamine, pyridine, dimethylphenylamine, dimethylbenzylamine or 1,4-dimethylpiperadine, and $Z^{-(n/a)}$ (hereinafter often simply described as Z) is chloro anion, perchlorate anion, or boron tetrafluoride anion.

Concrete examples of the quaternary ammonium salt used as a condensing agent in the present invention include 4-(4,6-dimethoxy-1,3,5-triazin-2-yl)-4-methylmorpholinium chloride, 4-(4,6-dimethoxy-1,3,5-triazin-2-yl)-4-methylmorpholinium perchlorate, 4-(4,6-dimethoxy-1,3,5-triazin-2-yl)-4-methylmorpholinium tetrafluoroborate, 4-(4,6-dimethoxy-1,3,5-triazin-2-yl)-4-methylmorpholinium chloride, 4-(4,6-diethoxy-1,3,5-triazin-2-yl)-4-methylmorpholinium chloride, 4-(4,6-diethoxy-1,3,5-triazin-2-yl)-4-methylmorpholinium perchlorate, 4-(4,6-diethoxy-1,3,5-triazin-2-yl)-4-methylmorpholinium tetrafluoroborate, 4-(4,6-di-n-propoxy-1,3,5-triazin-2-yl)-4-methylmorpholinium chloride, 4-(4,6-di-n-propoxy-1,3,5-triazin-2-yl)-4-methylmorpholinium perchlorate, 4-(4,6-di-n-propoxy-1,3,5-triazin-2-yl)-4-methylmorpholinium tetrafluoroborate, 4-(4,6-diphenoxy-1,3,5-triazin-2-yl)-4- methylmorpholinium chloride, 4-(4,6-diphenoxy-1,3,5-triazin-2-yl)-4-methylmorpholinium perchlorate, 4-(4,6-diphenoxy-1,3,5-triazin-2-yl)-4-methylmorpholinium tetrafluoroborate, 4-(4,6-dimethoxy-1,3,5-triazin-2-yl)-4-ethylmorpholinium chloride, 4-(4,6-dimethoxy-1,3,5-triazin-2-yl)-4-ethylmorpholinium perchlorate, 4-(4,6-dimethoxy-1,3,5-triazin-2-yl)-4-ethylmorpholinium tetrafluoroborate, 4-(4,6-diethoxy-1,3,5-triazin-2-yl)-4-ethylmorpholinium chloride, 4-(4,6-diethoxy-1,3,5-triazin-2-yl)-4-ethylmorpholinium perchlorate, 4-(4,6-diethoxy-1,3,5-triazin-2-yl)-4-ethylmorpholinium tetrafluoroborate, 4-(4,6-di-n-propoxy-1,3,5-triazin-2-yl)-4-ethylmorpholinium chloride, 4-(4,6-di-n-propoxy-1,3,5-triazin-2-yl)-4-ethylmorpholinium perchlorate, 4-(4,6-di-n-propoxy-1,3,5-triazin-2-yl)-4-ethylmorpholinium tetrafluoroborate, 4-(4,6-diphenoxy-1,3,5-triazin-2-yl)-4-ethylmorpholinium chloride, 4-(4,6-diphenoxy-1,3,5-triazin-2-yl)-4-ethylmorpholinium perchlorate, 4-(4,6-diphenoxy-1,3,5-triazin-2-yl)-4-ethylmorpholinium tetrafluoroborate, 1-(4,6-dimethoxy-1,3,5-triazin-2-yl)-1-methylpiperidinium chloride, 1-(4,6-dimethoxy-1,3,5-triazin-2-yl)-1-methylpiperidinium perchlorate, 1-(4,6-dimethoxy-1,3,5-triazin-2-yl)-1-methylpiperidinium tetrafluoroborate, 1-(4,6-dimethoxy-1,3,5-triazin-2-yl)-1-ethylpiperidinium chloride, 1-(4,6-dimethoxy-1,3,5-triazin-2-yl)-1-ethylpiperidinium perchlorate, 1-(4,6-dimethoxy-1,3,5-triazin-2-yl)-1-ethylpiperidinium tetrafluoroborate, 1-(4,6-dimethoxy-1,3,5-triazin-2-yl)-1-methylpyrrolidinium chloride, 1-(4,6-dimethoxy-1,3,5-triazin-2-yl)-1-methylpyrrolidinium perchlorate, 1-(4,6-dimethoxy-1,3,5-triazin-2-yl)-1-methylpyrrolidinium tetrafluoroborate, 1-(4,6-dimethoxy-1,3,5-triazin-2-yl)-1-ethylpyrrolidinium chloride, 1-(4,6-dimethoxy-1,3,5-triazin-2-yl)-1-ethylpyrrolidinium perchlorate, 1-(4,6-dimethoxy-1,3,5-triazin-2-yl)-1-ethylpyrrolidinium tetrafluoroborate, (4,6-dimethoxy-1,3,5-triazin-2-yl)triethylammonium perchlorate, (4,6-dimethoxy-1,3,5-triazin-2-yl)triethylammonium tetrafluoroborate, (4,6-dimethoxy-1,3,5-triazin-2-yl)dimethylcyclohexylammonium perchlorate, (4,6-dimethoxy-1,3,5-triazin-2-yl)dimethylcyclohexylammonium tetrafluoroborate, (4,6-dimethoxy-1,3,5-triazin-2-yl)pyridinium perchlorate, (4,6-dimethoxy-1,3,5-triazin-2-yl)pyridinium tetrafluoroborate, (4,6-diethoxy-1,3,5-triazin-2-yl)pyridinium perchlorate, (4,6-diethoxy-1,3,5-triazin-2-yl)pyridinium tetrafluoroborate, (4,6-dimethoxy-1,3,5-triazin-2-yl)dimethylphenylammonium perchlorate, (4,6-dimethoxy-1,3,5-triazin-2-yl)dimethylphenylammonium tetrafluoroborate, (4,6-diethoxy-1,3,5-triazin-2-yl)dimethylphenylammonium perchlorate, (4,6-diethoxy-1,3,5-triazin-2-yl)dimethylphenylammonium tetrafluoroborate, (4,6-dimethoxy-1,3,5-triazin-2-yl)dimethylbenzylammonium perchlorate, (4,6-dimethoxy-1,3,5-triazin-2-yl)dimethylbenzylammonium tetrafluoroborate, (4,6-diethoxy-1,3,5-triazin-2-yl)dimethylbenzylammonium perchlorate, (4,6-diethoxy-1,3,5-triazin-2-yl)dimethylbenzylammonium tetrafluoroborate, 1,4-di(4,6-dimethoxy-1,3,5-triazin-2-yl)-1,4-dimethylpiperadinium dichloride, 1,4-di(4,6-dimethoxy-1,3,5-triazin-2-yl)-1,4-dimethylpiperadinium diperchlorate, 1,4-di(4,6-dimethoxy-1,3,5-triazin-2-yl)-1,4-dimethylpiperadinium ditetrafluoroborate, 1,4-di(4,6-diethoxy-1,3,5-triazin-2-yl)-1,4-dimethylpiperadinium dichloride, 1,4-di(4,6-diethoxy-1,3,5-triazin-2-yl)-1,4-dimethylpiperadinium diperchlorate, 1,4-(4,6-diethoxy-1,3,5-triazin-2-yl)-1,4-dimethylpiperadinium ditetrafluoroborate, 1,4-di(4,6-di-n-propoxy-1,3,5-triazin-2-yl)-1,4-dimethylpiperadinium dichloride, 1,4-di(4,6-di-n-propoxy-1,3,5-triazin-2-yl)-1,4-dimethylpiperadinium diperchlorate, 1,4-di(4,6-di-n-propoxy-1,3,5-triazin-2-yl)-1,4-dimethylpiperadinium ditetrafluoroborate, 1,4-di(4,6-diphenoxy-1,3,5-triazin-2-yl)-1,4-dimethylpiperadinium dichloride, and 1,4-di(4,6-diphenoxy-1,3,5-triazin-2-yl)-1,4-dimethylpiperadinium diperchlorate.

Examples of the quaternary ammonium salt that can be favorably used for accomplishing a condensation yield include 4-(4,6-dimethoxy-1,3,5-triazin-2-yl)-4-methylmorpholinium chloride, 4-(4,6-dimethoxy-1,3,5-triazin-2-yl)-4-methylmorpholinium perchlorate, 4-(4,6-dimethoxy-1,3,5-triazin-2-yl)-4-methylmorpholinium tetrafluoroborate, 4-(4,6-diethoxy-1,3,5-triazin-2-yl)-4-methylmorpholinium chloride, 4-(4,6-diethoxy-1,3,5-triazin-2-yl)-4-methylmorpholinium perchlorate, 4-(4,6-diethoxy-1,3,5-triazin-2-yl)-4-methylmorpholinium tetrafluoroborate, 4-(4,6-dimethoxy-1,3,5-triazin-2-yl)-4-ethylmorpholinium chloride, 4-(4,6-dimethoxy-1,3,5-triazin-2-yl)-4-ethylmorpholinium perchlorate, 4-(4,6-dimethoxy-1,3,5-triazin-2-yl)-4-ethylmorpholinium tetrafluoroborate, 4-(4,6-diethoxy-1,3,5-triazin-2-yl)-4-ethylmorpholinium chloride, 4-(4,6-diethoxy-1,3,5-triazin-2-yl)-4-ethylmorpholinium perchlorate, 4-(4,6-diethoxy-1,3,5-triazin-2-yl)-4-ethylmorpholinium tetrafluoroborate, 1-(4,6-dimethoxy-1,3,5-triazin-2-yl)-1-methylpiperidinium chloride, 1-(4,6-dimethoxy-1,3,5-triazin-2-yl)-1-methylpiperidinium perchlorate, 1-(4,6-dimethoxy-1,3,5-triazin-2-yl)-1-methylpiperidinium tetrafluoroborate, 1-(4,6-dimethoxy-1,3,5-triazin-2-yl)-1-ethylpiperidinium chloride, 1-(4,6-dimethoxy-1,3,5-triazin-2-yl)-1-ethylpiperidinium perchlorate, 1-(4,6-dimethoxy-1,3,5-triazin-2-yl)-1-ethylpiperidinium tetrafluoroborate, 1-(4,6-dimethoxy-1,3,5-triazin-2-yl)-1-methylpyrrolidinium chloride, 1-(4,6-dimethoxy-1,3,5-triazin-2-yl)-1-methylpyrrolidinium perchlorate, 1-(4,6-dimethoxy-1,3,5-triazin-2-yl)-1-methylpyrrolidinium tetrafluoroborate, 1-(4,6-dimethoxy-1,3,5-triazin-2-yl)-1-ethylpyrrolidinium chloride, 1-(4,6-dimethoxy-1,3,5-triazin-2-yl)-1-ethylpyrrolidinium perchlorate, 1-(4,6-dimethoxy-1,3,5-triazin-2-yl)-1-ethylpyrrolidinium tetrafluoroborate, (4,6-dimethoxy-1,3,5-triazin-2-yl)pyridinium perchlorate, (4,6-dimethoxy-1,3,5-triazin-2-yl)pyridinium tetrafluoroborate, (4,6-diethoxy-1,3,5-triazin-2-yl)pyridinium perchlorate, 1,4-di(4,6-dimethoxy-1,3,5-triazin-2-yl)-1,4-dimethylpiperadinium dichloride, 1,4-di(4,6-dimethoxy-1,3,5-triazin-2-yl)-1,4-dimethylpiperadinium diperchlorate, 1,4-di(4,6-dimethoxy-1,3,5-triazin-2-yl)-1,4-dimethylpiperadinium ditetrafluoroborate, 1,4-di(4,6-diethoxy-1,3,5-triazin-2-yl)-1,4-dimethylpiperadinium dichloride, 1,4-di(4,6-diethoxy-1,3,5-triazin-2-yl)-1,4-dimethylpiperadinium diperchlorate, and 1,4-(4,6-diethoxy-1,3,5-triazin-2-yl)-1,4-dimethylpiperadinium ditetrafluoroborate.

In particular, the quaternary ammonium salts newly prepared by the present inventors are the ones represented by the above-mentioned general formula (III). In the formula, R1 and R2 are as described earlier, and in which a methyl group or an ethyl group is favorably used as an alkyl group, and a phenyl group is favorably used as an aryl group from the standpoint of easy synthesis.

Further, the group represented by —R3— in the general formula (III) is a group >C=O, a group —CH2—, or a group —CH(OH)—. Among such groups, the group represented by R3— is preferably a group —CH(OH)— from such a standpoint that the quaternary ammonium salt that is formed has a low hygroscopic property.

Further X– is chloro anion, perchlorate anion or boron tetrafluoride anion. Among them, chloro anion is preferably used from the standpoint of easy synthesis.

Concrete examples of the quaternary ammonium salt represented by the general formula (III) include 1-(4,6-dimethoxy-1,3,5-triazin-2-yl)quinuclidinium chloride, 1-(4,6-dimethoxy-1,3,5-triazin-2-yl)-3-hydroxyquinuclidinium chloride, 1-(4,6-dimethoxy-1,3,5-triazin-2-yl)-3-oxoquinuclidinium chloride, 1-(4,6-diethoxy-1,3,5-triazin-2-yl)quinuclidinium chloride, 1-(4,6-diethoxy-1,3,5-triazin-2-yl)-3-hydroxyquinuclidinium chloride, 1-(4,6-diethoxy-1,3,5-triazin-2-yl)-3-oxoquinuclidinium chloride, 1-(4,6-di-n-propoxy-1,3,5-triazin-2-yl)quinuclidinium chloride, 1-(4,6-di-n-propoxy-1,3,5-triazin-2-yl)-3-hydroxyquinuclidinium chloride, 1-(4,6-di-n-propoxy-1,3,5-triazin-2-yl)-3-oxoquinuclidinium chloride, 1-(4,6-diisopropoxy-1,3,5-triazin-2-yl)quinuclidinium chloride, 1-(4,6-diisopropoxy-1,3,5-triazin-2-yl)-3-hydroxyquinuclidinium chloride, 1-(4,6-diisopropoxy-1,3,5-triazin-2-yl)-3-oxoquinuclidinium chloride, 1-(4,6-di-n-butoxy-1,3,5-triazin-2-yl)quinuclidinium chloride, 1-(4,6-di-n-butoxy-1,3,5-triazin-2-yl)-3-hydroxyquinuclidinium chloride, 1-(4,6-di-n-butoxy-1,3,5-triazin-2-yl)-3-oxoquinuclidinium chloride, 1-(4,6-diphenoxy-1,3,5-triazin-2-yl)quinuclidinium chloride, 1-(4,6-diphenoxy-1,3,5-triazin-2-yl)-3-hydroxyquinuclidinium chloride, 1-(4,6-diphenoxy-1,3,5-triazin-2-yl)-3-oxoquinuclidinium chloride, as well as those quaternary ammonium salts of which chloro anions that are counter anions are exchanged with perchlorate anions or boron tetrafluoride anions.

Among them, it is particularly desired to use 1-(4,6-dimethoxy-1,3,5-triazin-2-yl)quinuclidinium chloride, 1-(4,6-dimethoxy-1,3,5-triazin-2-yl)-3-hydroxyquinuclidinium chloride, 1-(4,6-dimethoxy-1,3,5-triazin-2-yl)-3-oxoquinuclidinium chloride, 1-(4,6-diethoxy-1,3,5-triazin-2-yl)quinuclidinium chloride, 1-(4,6-diethoxy-1,3,5-triazin-2-yl)-3-hydroxyquinuclidinium chloride, 1-(4,6-diethoxy-1,3,5-triazin-2-yl)-3-oxoquinuclidinium chloride, 1-(4,6-diphenoxy-1,3,5-triazin-2-yl)quinuclidinium chloride, 1-(4,6-diphenoxy-1,3,5-triazin-2-yl)-3-hydroxyquinuclidinium chloride, 1-(4,6-diphenoxy-1,3,5-triazin-2-yl)-3-oxoquinuclidinium chloride, as well as those quaternary ammonium salts of which chloro anions that are counter anions are exchanged with perchlorate anions or boron tetrafluoride anions, since they can be easily synthesized and a high condensation yield is expected when they are used as condensing agents.

There is no particular limitation on the amount the quaternary ammonium salt represented by the above general formula (I) that is used as a condensing agent in the present invention, and the amount may be suitably determined depending upon the reaction system. When the amount of the condensing agent is too small, the condensation is not finished. When the amount of the condensing agent is too great, the reaction occurs with a compound having nucleophilic functional group such as amine compound, and the yield decreases. Upon taking such points into consideration, it is desired to use the condensing agent in an amount of from 0.9 to 3 mols, particularly, from 0.95 to 2.5 mols, particularly, from 0.95 to 1.3 mols and, more particularly, from 0.95 to 1.2 mols as a mole number of the quaternary nitrogen atoms in the quaternary ammonium salt of the general formula (I) per mol of the carboxylic acid compound.

The quaternary ammonium salts represented by the above general formula (I) of the invention can be prepared according to a known method. When Z in the general formula (I) is chloro anion, the quaternary ammonium salt of the general formula (I) can be prepared by reacting a triazine compound represented by the following general formula (IV),

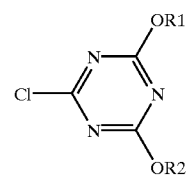

(IV)

wherein R1 and R2 are, independently from each other, alkyl groups having 1 to 4 carbon atoms or aryl groups having 6 to 8 carbon atoms,
with a tertiary amine in an organic solvent, and separating the precipitated crystals by filtering.

Further, when Z in the general formula (I) is perchlorate anion, the quaternary ammonium salt is prepared by adding sodium perchlorate in reacting the triazine compound represented by the above general formula (IV) with the tertiary amine in an organic solvent as disclosed in Japanese Unexamined Patent Publication No. 34634/1972.

When Z in the general formula (I) is boron tetrafluoride anion, the quaternary ammonium salt is prepared by adding sodium tetrafluoroborate in reacting the triazine compound represented by the above general formula (IV) with the tertiary amine in an organic solvent.

When the sodium perchlorate and the sodium tetrafluoroborate are used, the sodium chloride is formed as a by-product and is contained in the product in the step of separating the product by filtration. According to the present invention, however, there occurs no trouble even when the sodium chloride is mixed in the reaction system.

In the present invention, the quaternary ammonium salt of the general formula (III) is a novel compound and is useful as a condensing agent. Though there is no particular limitation on the preparation method, the quaternary ammonium salt is preferably prepared according to, for example, a method described below.

That is, the quaternary ammonium salt is preferably obtained by reacting a triazine derivative represented by the above-mentioned general formula (IV) with a quinuclidine derivative represented by the following general formula (V),

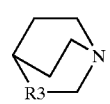

(V)

wherein a group represented by —R3— is the same as the group —R3— in the above-mentioned general formula (III).

Concrete examples of the triazine derivative represented by the above general formula (IV) that can be used for the preparation of the quaternary ammonium salt of the above general formula (I) include 2-chloro-4,6-diethoxy-1,3,5-triazine, 2-chloro-4,6-di-n-propoxy-1,3,5-triazine, 2-chloro-4,6-diisopropoxy-1,3,5-triazine, 2-chloro-4,6-di-n-butoxy-1,3,5-triazine, and 2-chloro-4,6-diphenoxy-1,3,5-triazine. Among them, there can be preferably used 2-chloro-4,6-dimethoxy-1,3,5-triazine, 2-chloro-4,6-diethoxy-1,3,5-triazine, and 2-chloro-4,6-diphenoxy-1,3,5-triazine that can be easily synthesized. Some of these triazine derivatives are available as industrial starting materials. Generally, however, they are obtained by reacting a cyanuric chloride with a corresponding alcohol in the presence of a potassium carbonate (or sodium hydrogen carbonate, etc.) and a phase-transfer catalyst.

The tertiary amine used for the preparation of the quaternary ammonium salt of the above-mentioned general formula (I) is the one in which E in the general formula (I) is as described above.

In particular, as the quinuclidine derivative of the general formula (V) which is the tertiary amine that can be used for the preparation of the novel quaternary ammonium salt represented by the above general formula (III), there can be exemplified quinuclidine, 3-quinuclidinol and 3-quinuclidinone. These quinuclidine derivatives are all easily available as reagents and industrial starting materials.

The reaction of the triazine derivative represented by the general formula (IV) with the tertiary amine easily proceeds upon mixing the two together. Here, it is desired to use an organic solvent.

Any organic solvent can be used without any limitation provided it does not inhibit the reaction. Concrete examples of the organic solvent that can be used for the reaction include ethers such as tetrahydrofurane, 1-4-dioxane, diethyl ether and diisopropyl ether; halogenated aliphatic hydrocarbons such a methylene chloride, chloroform and carbon tetrachloride; esters such as ethyl acetate and propyl acetate; ketones such as acetone, methyl ethyl ketone and methyl isobutyl ketone; nitrites such as acetonitrile and propylonitrile; aromatic hydrocarbons such as benzene, toluene and xylene; halogenated aromatic hydrocarbons such as chlorobenzene and dichlorobenzene; amides such as N,N-dimethylformamide and N,N-dimethyllacetamide; aliphatic hydrocarbons such as hexane and heptane; carbonates such as dimethyl carbonate; alcohols such as t-butyl alcohol and t-amyl alcohol; and dimethyl sulfoxide.

Among them, there can be preferably used organic solvents with which a high isolation yield can be expected, i.e., ethers such as tetrahydrofuran, 1,4-dioxane, diethyl ether and diisopropyl ether; halogenated aliphatic hydrocarbons such as methylene chloride and chloroform; esters such as ethyl acetate and propyl acetate; ketones such as acetone, methyl ethyl ketone and methyl isobutyl ketone; nitrites such as acetonitrile and propylonitrile; aromatic hydrocarbons such as benzene, toluene and xylene; and carbonates such as dimethyl carbonate.

There is no particular limitation on the amount of the solvent used in the reaction. When the amount is too large, however, the yield decreases per a batch, which is not economical. When the amount is too small, on the other hand, stirring is impaired. Therefore, the amount of the solvent is so selected that the concentration of the quaternary ammonium salt of the invention that is formed is from 0.1 to 60% by weight and, preferably, from 1 to 50% by weight.

The ratio of the triazine derivative represented by the above general formula (IV) and the tertiary amine used in the above reaction is 1 to 1 in terms of a molar ratio, since the reaction is a stoichiometric reaction. Generally, however, either one is used in a slightly excess amount to complete the reaction. It is usually desired that the tertiary amine is used in a range of from 0.7 to 1.3 moles and, preferably, from 0.8 to 1.2 moles per a mole of the triazine derivative represented by the general formula (IV).

There is no particular limitation on the temperature of the reaction. When the temperature is too low, the reaction rate becomes small and when the temperature is too high, the side reaction is promoted. Usually, therefore, the temperature is selected from –20 to 70° C. and, preferably, from –10 to 60° C.

The reaction is usually carried out in the atmosphere. However, since some compounds may have hygroscopic property, it is generally desired to conduct the reaction in the dry air that has passed through a drying tube such as a calcium chloride tube or in an inert gas atmosphere such as of nitrogen, helium or argon. The reaction is conducted under any condition such as a reduced pressure condition, a normal pressure condition or a elevated pressure condition.

Though there is no particular limitation on the reaction time, the time of from 0.1 to 10 hours is usually sufficient. The kind of the counter anion may be changed at this moment by the above-mentioned method. The thus formed quaternary ammonium salt represented by the above general formula (I) usually precipitates in the form of crystals. Therefore, the quaternary ammonium salt is separated in a solid form by an ordinary solid-liquid separation method such as centrifuge, centrifugal filtration, compressed filtration or reduced pressure filtration, followed by drying under a reduced pressure. When no crystal precipitates, the organic solvent that is used is removed as much as possible, a solvent such as tetrahydrofurane or the like is added to precipitate the crystals which are then obtained by the method same as the one described above.

The structure of the thus obtained quaternary ammonium salt can be confirmed by means ① to ④ described below.

① The mode of bonding of hydrogen atoms existing in the quaternary ammonium salt of the invention can be learned by measuring a $^1$H-nuclear magnetic resonance spectrum ($^1$H-NMR).

② Characteristic absorption due to functional groups in the quaternary ammonium salt of the invention can be observed by measuring an infrared absorption spectrum (IR).

③ The mode of bonding of atomic groups in the molecules of the compound put to the measurement can be learned by measuring a mass spectrum (MS) and by calculating the observed peaks (generally, composition formulas corresponding to values m/e obtained by dividing the mass number m of an ion by a charge number e of the ion).

④ Weight percents of carbon, hydrogen, nitrogen and chlorine can be found by the elemental analysis. The weight percent of oxygen is calculated by subtracting the sum of weight percents of the elements that are perceived from 100.

<Preparation of Carboxylic Acid Derivatives>

The quaternary ammonium salt represented by the above general formula (I) can be favorably used as a condensing agent in preparing carboxylic acid derivatives from a carboxylic acid compound and a compound having a nucleophilic functional group such as a group —OH, a group —SH or a group >NH. In particular, it can be preferably used as a condensing agent in preparing an amide compound by reacting a carboxylic acid compound with an amine compound, or in preparing an ester compound by reacting a carboxylic acid compound with an alcohol compound.

Described below is a method of preparing these compounds using the above quaternary ammonium salt as a condensing agent.

(1) A method of preparing an amide compound by reacting a carboxylic acid compound with an amine compound by using a quaternary ammonium salt represented by the above general formula (I) as a condensing agent (hereinafter also referred to as a method of preparing an amide of the present invention).

According to the method of preparing an amide of the present invention, features reside in that the reaction yield is further improved and the reaction time is shortened even when quaternary ammonium salts which have not been known to exhibit the function as condensing agents, inclusive of the novel quaternary ammonium salt, are used as condensing agents, and when a quaternary ammonium salt (concretely, 4-(4,6-dimethoxy-1,3,5-triazin-2-yl)-4- methylmorpholinium salt) that has been known as a condensing agent, is used.

Concerning the latter point, a general condensing agent of the type that activates the carboxylic acid compound, that is usually used, reacts with the amine compound when it is made present in its own form, and loses the activity of the condensing agent or the activity extinguishes. Generally, therefore, the condensing agent is reacted with a carboxylic acid compound in advance to form a reactive derivative which is, then reacted with an amine compound as is done by a method employed by Kaminski et al mentioned earlier.

According to the study conducted by the present inventors, on the other hand, it was clarified that the quaternary ammonium salt represented by the general formula (I) exhibits a high condensing activity even when it is made present together with the amine compound, permits the presence of three kinds of reaction reagents, i.e., quaternary ammonium salt, carboxylic acid compound and amine compound (compound having a nucleophilic functional group) to exhibit the above-mentioned effects, i.e., improved reaction yield and shortened reaction time.

The method of preparing amides of the present invention is conducted in the same manner as the conventional method of using a condensing agent, but using the quaternary ammonium salt represented by the above general formula (I) as a condensing agent. For example, the quaternary ammonium salt represented by the above general formula (I) is reacted with a carboxylic acid compound, followed by the reaction with an amine compound. According to the method of preparing amides of the invention, further, the above-mentioned three kinds of reaction reagents may be mixed together and reacted without forming reactive derivatives by utilizing the above-mentioned peculiar properties of the quaternary ammonium salt that is used. It can be said that the latter method is particularly preferred since it enhances the reaction yield, shortens the reaction time, and makes it possible to eliminate the step of forming reactive derivatives.

In the method of preparing amides of the present invention, there is no particular limitation on the kind and amount of the quaternary ammonium salt of the invention that is used as a condensing agent, and its amount may be suitably determined depending upon the reaction system. It is desired that the quaternary ammonium salts used in the preparation method are those that are described above featuring easy synthesis and making it possible to expect a high condensation yield when they are used as condensing agents. When the amount of the condensing agent is too small, the condensing reaction is not finished and when its amount is too large, reaction takes place with the amine compound to deteriorate the yield. It is, therefore, desired that the condensing agent is used in an amount of from 0.9 to 1.3 moles and, particularly, from 0.95 to 1.2 moles per a mole of the carboxylic acid compound.

Next, described below is a carboxylic acid compound that is used in the method of preparing amides of the present invention.

As the carboxylic acid compound used for the method of preparing amides of the present invention, any carboxylic acid having a carboxyl group can be used without limitation.

Concrete examples of the compound include aliphatic carboxylic acid compounds such as acetic acid, propionic acid, 2,2-dimethylpropionic acid, butanoic acid, pentanoic acid, hexanoic acid, heptanoic acid, octanoic acid, nonanoic acid, decanoic acid, undecanoic acid, acrylic acid and methacrylic acid; aromatic carboxylic acid compounds such as benzoic acid, o-nitrobenzoic acid, m-nitrobenzoic acid, p-nitrobenzoic acid, o-chlorobenzoic acid, m-chlorobenzoic acid, p-chlorobenzoic acid, o-methoxybenzoic acid, m-methoxybenzoic acid, p-methoxybenzoic acid, 3-phenylpropionic acid, 3-phenyl-2-propenoic acid, 2-(4-methoxyphenyl)acetic acid, and 3-(4-hydroxyphenyl) propionic acid; and 2-aminothiazolylacetic acid derivatives and amino acid derivatives of which the amino group is protected.

Among these carboxylic acid compounds, it is desired to use 2-aminothiazolylacetic acid derivatives represented by the following general formula (VI),

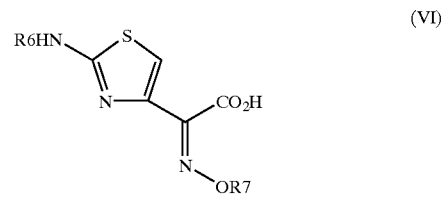

(VI)

wherein R6 is a hydrogen atom or an acyl group, an alkoxycarbonyl group, an aralkyloxycarbonyl group or an aralkyl group, and R7 is a hydrogen atom, an alkyl group, an aralkyl group, an acyl group or an alkoxycarbonylalkyl group, to obtain a cephem compound which is very useful as an amide compound, as a cephalosporin antibiotic or as a precursor thereof.

Here, the cephem compound generally stands for a compound having a cephalosporanic acid in the molecules thereof. When a carboxylic acid compound comprising the above-mentioned 2-aminothiazolylacetic acid derivatives is reacted with an amine compound comprising 7-aminocephalosporanic acid derivatives that will be described later, it is allowed to prepare a cephem compound having a structure corresponding to the starting materials as an amide compound.

In the above general formula (VI), any of acyl group, alkoxycarbonyl group, aralkyloxycarbonyl group or aralkyl group represented by R6 can be used without limitation provided it can be easily dropped off. Concrete examples of these groups are as described below. Examples of the acyl group are those groups having 1 to 5 carbon atoms, such as formyl group, acetyl group, butyryl group, isobutyryl group, valeryl group and pivaloyl group; examples of the alkoxycarbonyl group include those groups having 2 to 7 carbon atoms, such as methoxycarbonyl group, ethoxycarbonyl group, propoxycarbonyl group, isopropoxycarbonyl group, tert-butoxycarbonyl group and tert-amyloxycarbonyl group; and examples of the aralkyloxycarbonyl group include those groups having 8 to 10 carbon atoms, such as benzyloxycarbonyl group and phenetyloxycarbonyl group. Examples of the aralkyl group include those groups having 7 to 20 carbon atoms, such as benzyl group, diphenylmethyl group and triphenylmethyl group.

Among them, particularly preferred examples of the acyl group are formyl group and acetyl group, particularly preferred examples of the alkoxycarbonyl group are methoxycarbonyl group and tert-butoxycarbonyl group, particularly preferred example of the aralkyloxycarbonyl group is benzyloxycarbonyl group, and particularly preferred examples of the aralkyl group are benzyl group and triphenylmethyl group from the standpoint of easy elimination reaction and a high condensation yield.

As the alkyl group, aralkyl group, acyl group or alkoxycarbonylalkyl group represented by R7, there can be used, without limitation, any group that develops a pharmacological effect as a cephem compound or there can be used any hydrocarbon group that can be easily dropped off. Concrete examples are as described below. Examples of the alkyl group include lower alkyl group having 1 to 4 carbon atoms, such as methyl group, ethyl group, propyl group, isopropyl group, butyl group, isobutyl group and tert-butyl group; examples of the aralkyl group include those groups having 7 to 20 carbon atoms, such as benzyl group, diphenyl methyl group, and triphenylmethyl group; examples of the acyl group include those groups having 1 to 5 carbon atoms, such as formyl group, acetyl group, butyryl group, isobutyryl group, valeryl group and pivaloyl group; and examples of the alkoxycarbonylalkyl group include those groups having 3 to 8 carbon atoms, such as methoxycarbonylmethyl group, 1-methoxycarbonyl-1-methyl ethyl group, tert-butoxycarbonylmethyl group and 1-tert-butoxycarbonyl-1-methyl ethyl group. Among them, there is preferably used an alkyl group having 1 to 3 carbon atoms having less steric hindrance, such as methyl group, ethyl group or propyl group.

Among the 2-aminothiazolylacetic acid derivatives represented by the general formula (VI), it is desired to use those in which R6 is a hydrogen atom, a benzyloxycarbonyl group, a tert-butoxycarbonyl group, a methoxycarbonyl group, a formyl group, a trityl group, an acetyl group or a chloroacetyl group, and R7 is a hydrogen atom, a methyl group, an ethyl group, a methoxycarbonylmethyl group, a 1-methoxycarbonyl-1-methyl ethyl group or a benzyl group from the standpoint of expecting a high pharmacological effect when they are transformed into a cephem compound in preparing a cephem compound.

Concrete examples of the 2-aminothiazolylacetic acid ester derivatives represented by the above general formula (VI) that can be preferably used, include 2-(2-aminothiazolyl-4-yl)-2-methoxyiminoacetic acid, 2-(2-benzyloxycarbonylaminothiazolyl-4-yl)-2-methoxyiminoacetic acid, 2-(2-tert-butoxycarbonylaminothiazolyl-4-yl)-2-methoxyiminoacetic acid, 2-(2-methoxycarbonylaminothiazolyl-4-yl)-2-methoxyiminoacetic acid, 2-(2-formylaminothiazolyl-4-yl)-2-methoxyiminoacetic acid, 2-(2-tritylaminothiazolyl-4-yl)-2-methoxyiminoacetic acid, 2-(2-acetylaminothiazolyl-4-yl)-2-methoxyiminoacetic acid, 2-(2-chloroacetylaminothiazolyl-4-yl)-2-methoxyiminoacetic acid, 2-(2-aminothiazolyl-4-yl)-2-hydroxyiminoacetic acid, 2-(2-benzyloxycarbonylaminothiazolyl-4-yl)-2-hydroxyiminoacetic acid, 2-(2-tert-butoxycarbonylaminothiazolyl-4-yl)-2-hydroxyiminoacetic acid, 2-(2-methoxycarbonylaminothiazolyl-4-yl)-2-hydroxyiminoacetic acid, 2-(2-formylaminothiazolyl-4-yl)-2-hydroxyiminoacetic acid, 2-(2-tritylaminothiazolyl-4-yl)-2-hydroxyiminoacetic acid, 2-(2-acetylaminothiazolyl-4-yl)-2-hydroxyiminoacetic acid, 2-(2-aminothiazolyl-4-yl)-2-methoxycarbonylmethoxyiminoacetic acid, 2-(2-benzyloxycarbonylaminothiazolyl-4-yl)-2-methoxycarbonylmethoxyiminoacetic acid, 2-(2-tert-butoxycarbonylaminothiazolyl-4-yl)-2-methoxycarbonylmethoxyiminoacetic acid, 2-(2-methoxycarbonylaminothiazolyl-4-yl)-2-methoxycarbonylmethoxyiminoacetic acid, 2-(2-formylaminothiazolyl-4-yl)-2-methoxycarbonylmethoxyiminoacetic acid, 2-(2-tritylaminothiazolyl-4-yl)-2-methoxycarbonylmethoxyiminoacetic acid, 2-(2-acetylaminothiazolyl-4-yl)-2-methoxycarbonylmethoxyiminoacetic acid, 2-(2-chloroacetylaminothiazolyl-4-yl)-2-methoxycarbonylmethoxyiminoacetic acid, 2-(2-aminothiazolyl-4-yl)-2-(1-methoxycarbonyl-1-methylethoxy)iminoacetic acid, 2-(2-benzyloxycarbonylaminothiazolyl-4-yl)-2-(1-methoxycarbonyl-1-methylethoxy)iminoacetic acid, 2-(2-tert-butoxycarbonylaminothiazolyl-4-yl)-2-(1-methoxycarbonyl-l-methylethoxy)iminoacetic acid, 2-(2-methoxycarbonylaminothiazolyl-4-yl)-2-(1-methoxycarbonyl-1-methylethoxy)iminoacetic acid, 2-(2-formylaminothiazolyl-4-yl)-2-(1-methoxycarbonyl-1-methylethoxy)iminoacetic acid, 2-(2-tritylaminothiazolyl-4-yl)-2-(1-methoxycarbonyl-1-methylethoxy)iminoacetic acid, 2-(2-acetylaminothiazolyl-4-yl)-2-(1-methoxycarbonyl-1-methylethoxy)iminoacetic acid, 2-(2-aminothiazolyl-4-yl)-2-benzyloxyiminoacetic acid, 2-(2-benzyloxycarbonylaminothiazolyl-4-yl)-2-benzyloxyiminoacetic acid, 2-(2-tert-butoxycarbonylaminothiazolyl-4-yl)-2-benzyloxyiminoacetic acid, 2-(2-methoxycarbonylaminothiazolyl-4-yl)-2-benzyloxyiminoacetic acid, 2-(2-formylaminothiazolyl-4-yl)-2-benzyloxyiminoacetic acid, 2-(2-tritylaminothiazolyl-4-yl)-2-benzyloxyiminoacetic acid, 2-(2-acetylaminothiazolyl-4-yl)-2-benzyloxyiminoacetic acid, 2-(2-aminothiazolyl-4-yl)-2-ethoxyiminoacetic acid, 2-(2-benzyloxycarbonylaminothiazolyl-4-yl)-2-ethoxyiminoacetic acid, 2-(2-tert-butoxycarbonylaminothiazolyl-4-yl)-2-ethoxyiminoacetic acid, 2-(2-methoxycarbonylaminothiazolyl-4-yl)-2-ethoxyiminoacetic acid, 2-(2-formylaminothiazolyl-4-yl)-2-ethoxyiminoacetic acid, 2-(2-tritylaminothiazolyl-4-yl)-2-ethoxyiminoacetic acid, 2-(2-acetylaminothiazolyl-4-yl)-2-ethoxyiminoacetic acid, 2-(2-chloroacetylaminothiazolyl-4-yl)-2-ethoxyiminoacetic acid, and the like.

Among them, it is desired, for accomplishing high condensation yields, to use 2-(2-aminothiazolyl-4-yl)-2-methoxyiminoacetic acid, 2-(2-benzyloxycarbonylaminothiazolyl-4-yl)-2-methoxyiminoacetic acid, 2-(2-tert-butoxycarbonylaminothiazolyl-4-yl)-2-methoxyiminoacetic acid, 2-(2-methoxycarbonylaminothiazolyl-4-yl)-2-methoxyiminoacetic acid, 2-(2-formylaminothiazolyl-4-yl)-2-methoxyiminoacetic acid, 2-(2-tritylaminothiazolyl-4-yl)-2-methoxyiminoacetic acid, 2-(2-acetylaminothiazolyl-4-yl)-2-methoxyiminoacetic acid, 2-(2-chloroacetylaminothiazolyl-4-yl)-2-methoxyiminoacetic acid, 2-(2-aminothiazolyl-4-yl)-2-methoxycarbonylmethoxyiminoacetic acid, 2-(2-benzyloxycarbonylaminothiazolyl-4-yl)-2-methoxycarbonylmethoxyiminoacetic acid, 2-(2-tert-butoxycarbonylaminothiazolyl-4-yl)-2-methoxycarbonylmethoxyiminoacetic acid, 2-(2-methoxycarbonylaminothiazolyl-4-yl)-2-methoxycarbonylmethoxyiminoacetic acid, 2-(2-formylaminothiazolyl-4-yl)-2-methoxycarbonylmethoxyiminoacetic acid, 2-(2-acetylaminothiazolyl-4-yl)-2-methoxycarbonylmethoxyiminoacetic acid, 2-(2-aminothiazolyl-4-yl)-2-(1-methoxycarbonyl-1-methylethoxy)iminoacetic acid, 2-(2-benzyloxycarbonylaminothiazolyl-4-yl)-2-(1-methoxycarbonyl-1-methylethoxy)iminoacetic acid, 2-(2-tert-butoxycarbonylaminothiazolyl-4-yl)-2-(1-methoxycarbonyl-1-methylethoxy)iminoacetic acid, 2-(2-methoxycarbonylaminothiazolyl-4-yl)-2-(1-methoxycarbonyl-1-methylethoxy)iminoacetic acid, 2-(2-formylaminothiazolyl-4-yl)-2-(1-methoxycarbonyl-1- methylethoxy)iminoacetic acid, 2-(2-tritylaminothiazolyl-4-yl)-2-(1-methoxycarbonyl-1-methylethoxy)iminoacetic acid, 2-(2-aminothiazolyl-4-yl)-2-benzyloxyiminoacetic acid, 2-(2-benzyloxycarbonylaminothiazolyl-4-yl)-2-benzyloxyiminoacetic acid, 2-(2-tert-butoxycarbonylaminothiazolyl-4-yl)-2-benzyloxyiminoacetic acid, 2-(2-methoxycarbonylaminothiazolyl-4-yl)-2-benzyloxyiminoacetic acid, 2-(2-formylaminothiazolyl-4-yl)-2-benzyloxyiminoacetic acid, 2-(2-acetylaminothiazolyl-4-yl)-2-benzyloxyiminoacetic acid, 2-(2-aminothiazolyl-4-yl)-2-ethoxyiminoacetic acid, 2-(2-benzyloxycarbonylaminothiazolyl-4-yl)-2-ethoxyiminoacetic acid, 2-(2-tert-butoxycarbonylaminothiazolyl-4-yl)-2-ethoxyiminoacetic acid, 2-(2-methoxycarbonylaminothiazolyl-4-yl)-2-ethoxyiminoacetic acid, 2-(2-formylaminothiazolyl-4-yl)-2-ethoxyiminoacetic acid, 2-(2-tritylaminothiazolyl-4-yl)-2-ethoxyiminoacetic acid, and 2-(2-acetylaminothiazolyl-4-yl)-2-ethoxyiminoacetic acid.

As for the 2-aminothiazolylacetic acid ester derivatives represented by the above general formula (VI), there theoretically exist two kinds of isomers of syn(Z)-forms and anti(E)-forms concerning the oxyimino groups. Both of them can be used in the present invention. When used for the 7-aminocephalosporanoic acid derivatives, syn-forms exhibit higher pharmacological activity and are desired.

These 2-aminothiazolylacetic acid derivatives can be easily synthesized from the starting materials that are industrially available. They are prepared by, for example, using, as a starting material, a 2-aminothiazolylacetic acid ester compound which is available as a reagent or as an industrial starting material, such as ethyl 2-(2-aminothiazolyl-4-yl)-2-methoxyiminoacetate, ethyl 2-(2-aminothiazolyl-4-yl)-2-hydroxyiminoacetate, ethyl 2-(2-aminothiazolyl-4-yl)-2-1-methoxycarbonyl-1-methylethoxyiminoacetate or ethyl 2-(2-aminothiazolyl-4-yl)-2-methoxycarbonylmethoxyiminoacetate, and, as required, acting upon them an amino group-protecting agent such as acetyl chloride, chloroacetyl chloride, trityl chloride, benzyloxycarbonyl chloride, methoxycarbonyl chloride, di-tert-butyl dicarbonate, methyl formate or ethyl formate to protect the amino group and, further, as required, protecting the hydroxyimino group by using a hydroxy group-protecting agent such as dimethylsulfuric acid, diethylsulfuric acid, benzyl chloride or benzyl bromide, followed by hydrolysis.

When it is intended to obtain a peptide compound which is a very important compound as an intermediate product of medicine by the method of preparing amides of the invention, it is desired to use, as a carboxylic acid compound, an amino acid compound derivative of which the amino group is protected.

A peptide compound generally stands for a compound having two or more amino acid in the molecules thereof. When use is made of an amino acid compound derivative of which the amino group is protected as a carboxylic acid compound and an amino acid derivative of which the carboxyl group is protected as an amine compound, there can be prepared, as an amide compound, a peptide compound having a structure corresponding to the starting materials.

As the amino acid compound derivative of which the amino group is protected, there can be used any compound which has an amino group and a carboxyl group in the molecules and of which the amino group is protected by a protection group without limitation. Generally, however, there is used a compound of which the amino group of amino acid is protected, that is easily available as a reagent or as an industrial starting material.

Examples of the protection group include formyl group, acetyl group, benzoyl group, benzyloxycarbonyl group, tert-butoxycarbonyl group, allyoxycarbonyl group, methoxycarbonyl group, trityl group and fluorenylmethoxycarbonyl group.

Concrete examples of the amino acid compound derivative of which the amino group is protected and which can be favorably used for preparing peptide compounds include those compounds of which the amino group is protected by the above protection group, such as α-aminobutanoic acid, a-methylalanine, N-methylalanine, β-alanine, γ-aminobutanoic acid, 5-aminopentanoic acid, 6-aminohexanoic acid, 7-aminohexanoic acid, 8-aminooctanoic acid, 11-aminoundecanoic acid, 12-aminoundecanoic acid, alginine, asparagine, aspartic acid, β-cyclohexylalanine, cyclohexylglycine, S-acetamidecysteine, S-tert-butylcysteine, S-ethylthiosysteine, S-p-methoxybenzylcysteine, S-tritylcysteine, S-p-methylbenzylhomocysteine, glutamine, N-γ-ethylglutamine, N-γ-tritylglutamine, glutamic acid, isoglutamine, glycine, N-methylglycine, histidine, π-benzyloxymethylhistidine, 1-methylhistidine, 3-methylhistidine, isoleucine, leucine, N-methylleucine, lizine, N-ε-acetyllizine, N-ε-formylleucine, N-ε-benzyloxycarbonylleucine, methionine, norleucine, norvaline, ornithine, 4-benzoylphenylalanine, phenylalanine, 4-chlorophenylalanine, 4-fluorophenylalanine, 4-benzyloxycarbonylaminophenylalanine, homophenylalanine, phenylglycine, 4-hydroxyphenylglycine, proline, homoproline, 4-hydroxyproline, O-benzylhydroxyproline, N-methylglycine, homoserine, O-benzylhomoserine, O-benzylserine, serine, O-tert-butylserine, O-methylserine, threonine, O-benzylthreonine, tryptophan, tyrosine, O-tert-butyltyrosine, O-benzyltyrosine and valine.

Quite a few of the above amino acids have asymmetric carbons. In the present invention, L-forms, D-forms and a mixture thereof can be used without limitation.

These compounds are usually available as reagents and industrial starting materials. When not available, however, the compound may be prepared by protecting the amino acid in an organic solvent by using an amino group-protecting agent such as methyl formate, ethyl formate, acetyl chloride, anhydrous acetic acid, benzoyl chloride, benzyloxycarbonyl chloride, di-tert-butoxycarbonyl dicarbonate, di-tert-butoxycarbonyl fluoride, diallyloxycarbonyl dicarbonate, methoxycarbonyl chloride, trityl chloride or fluorenyl-methoxycarbonyl chloride after having added a tertiary amine such as methylmorpholine or triethylamine, followed by neutralization and crystallization.

Next, described below are the amine compounds used in the method of preparing amides of the present invention.

As the amine compounds used in the invention, there can be used any compound having primary and secondary amino groups without limitation.

Concrete examples of the amine compound used in the method of preparing amides of the invention include aliphatic amine compounds such as ethylamine, 1-propylamine, isopropylamine, 1-butylamine, isobutylamine, sec-butylamine, 1,2-dimethylpropylamine, tert-butylamine, 1-pentylamine, 1-hexylamine, 2-ethylhexylamine, 1-heptylamine, 1-octylamine, 1-nonylamine, 1-decanylamine, 1-undecanylamine, dimethylamine, diethylamine, diisopropylamine, allylamine, diallylamine, pyrrolidine, 3-hydroxypyrrolidine, piperidine, 2-pipecoline, 3-pipecoline, 4-pipecoline, 2,4-lupetidine, 2,6-lupetidine, 3,5-lupetidine, N-methylhomopiperazine, N-actylhomopiperazine, N-methylpiperazine, N-ethoxycarbonylpiperazine, p-chlorophenylpiperazine, 1-(2-pyrimidyl)piperazine, 1-amino-4-cyclohexylpiperazine, 1-cyclohexylpiperazine, 3-hydroxymethylpiperizine, N-aminopiperizine, N-aminopipecoline, 2-hydroxyethylpipecoline, hydroxyethylamine, 3-hydroxypropylamine, 2-hydroxypropylamine, 1-hydroxy-2-propylamine, 3-methoxypropylamine, 3-ethoxypropylamine, 3-butoxypropylamine, 3-(2-ethylhexyloxy)propylamine, 3-decyloxypropylamine, 3-lauroxypropylamine, 3-myristyloxypropylamine, dimethylaminoethylamine, diethylaminoethylamine, dimethylaminopropylamine, dibutylaminopropylamine, dimethylaminoethoxypropylamine and methoxyamine; aromatic amine compounds such as aniline, benzylamine, dibenzylamine, α-phenetylamine, β-phenetylamine, 2-aminothiazolyl, 2-aminopyridine, 3-aminopyridine, 4-aminopyridine, indole, N-(2-pyridyl)piperazine, furfurylamine, 2-aminopirazine, 2-amino-5-methylpyridine, 2-amino-6-methylpyridine, and 2-amino-4,6-dimethylpyridine; 7-aminocephalosporanic acid derivatives; and amino acid derivatives of which the carboxyl group is protected.

Among these amine compounds, it is desired to use 7-aminocephalosporanic acid derivatives to obtain cephem compounds. The 7-aminocephalosporanic acid derivatives that can be favorably used are the compounds represented by the following general formula (VII),

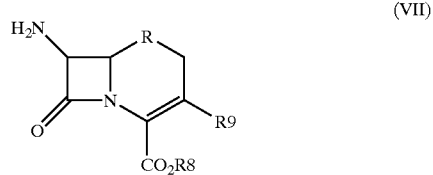

wherein R8 is an alkyl group, an aralkyl group, an aryl group, an alkoxycarbonylalkyl group, an alkoxycarbonyloxyalkyl group, an alkylcarbonyloxyalkyl group or a trialkylsilyl group, and R9 is a hydrogen atom, a methoxymethyl group, a chlorine atom, an iodomethyl group, a vinyl group, an acetyloxymethyl group, a 2-furalcarbonylthiomethyl group, a (1,2,3-thiadiazolyl-5-yl)thiomethyl group, a (1-methyltetrazolyl-5-yl)thiomethyl group, a (5-methyltetrazolyl-3-yl)methyl group, a (Z)-2-(1,2,3-thiadiazolyl-4-yl)ethenyl group, a (Z)-2-(4-methylthiazolyl-5-yl)ethenyl group, or a (1H-1,2,3-triazolyl-5-yl)thiomethylthio group.

As the alkyl group, aralkyl group, aryl group, alkoxycarbonylalkyl group, alkoxycarbonyloxyalkyl group, alkylcarbonyloxyalkyl group or trialkylsilyl group represented by R8 in the above general formula (VII), there can be used any group that can be easily hydrolyzed without limitation. Described below are concrete examples of these groups. Namely, preferred examples of the alkyl group are lower alkyl groups having 1 to 4 carbon atoms, such as methyl group, ethyl group, propyl group, isopropyl group, butyl group, isobutyl group, and tert-butyl group; preferred examples of the aralkyl group are those groups having 7 to 20 carbon atoms, such as benzyl group, diphenylmethyl group and triphenylmethyl group; preferred examples of the aryl group are those groups having 6 to 8 carbon atoms, such as phenyl group and tolyl group; preferred examples of the alkoxycarbonylalkyl group are methoxycarbonylmethyl group, 1-methoxycarbonyl-1-methylethyl group and tert-butoxycarbonylmethyl group; preferred examples of the alkoxycarbonyloxyalkyl group are those groups having 3 to 10 carbon atoms, such as 1-tert-butoxycarbonyloxyethyl group, 1-cyclohexyloxycarbonyloxyethyl group and 1-ethoxycarbonyloxyethyl group; preferred examples of the alkylcarbonyloxyalkyl group are those groups having 3 to carbon atoms, such as methylcarbonyloxymethyl group, ethylcarbonyloxymethyl group, and tert-butylcarbonyloxymethyl group; and preferred examples of the trialkylsilyl group are those groups having 3 to 9 carbon atoms, such as trimethylsilyl group, triethylsilyl group, and tert-butyldimethylsilyl group.

Among these groups, however, it is desired, from the standpoint of easy chemical or physiological hydrolysis, that the alkyl groups are lower alkyl groups having 1 to 4 carbon atoms, such as methyl group, ethyl group, propyl group, isopropyl group, butyl group, isobutyl group and tert-butyl group; the alkoxycarbonylalkyl groups are methoxycarbonylmethyl group, 1-methoxycarbonyl-1-methylethyl group, and tert-butoxycarbonylmethyl group; the alkoxycarbonyloxyalkyl groups are those groups having 3 to 10 carbon atoms, such as 1-tert-butoxycarbonyloxyethyl group, 1-cyclohexylcarbonyloxyethyl group and 1-ethoxycarbonyloxyethyl group; and the trialkylsilyl groups are those groups having 3 to 9 carbon atoms, such as trimethylsilyl group, triethylsilyl group and t-butyldimethylsilyl group.

Concrete examples of the 7-aminocephalosporanic acid derivative represented by the above general formula (VII) that can be favorably used include methyl 7-amino-3-cephem-4-carboxylate, methyl 7-amino-3-chloro-3-cephem-4-carboxylate, methyl 7-amino-3-iodomethyl-3-cephem-4-carboxylate, methyl 7-amino-3-vinyl-3-cephem-4-carboxylate, methyl 7-amino-3-actyloxymethyl-3-cephem-4-carboxylate, methyl 7-amino-3-(2-furalcarbonylthiomethyl)-3-cephem-4-carboxylate, methyl 7-amino-3-[(1,2,3-thiadiazolyl-5-yl)thiomethyl]-3-cephem-4-carboxylate, methyl 7-amino-3-[(1-methyltetrazolyl-5-yl)thiomethyl]-3-cephem-4-carboxylate, methyl 7-amino-3-[(Z)-2-(1,2,3-thiadiazolyl-4-yl)ethenyl]-3-cephem-4-carboxylate, methyl 7-amino-3-[(5-methyltetrazolyl-3-yl)methyl]-3-cephem-4-carboxylate, methyl 7-amino-3-[(Z)-2 (4-methylthiazolyl-5-yl)ethenyl]-3-cephem-4-carboxylate, methyl 7-amino-3-[(1H-1,2,3-triazolyl-5-yl)thiomethylthio]-3-cephem-4-carboxylate, ethyl 7-amino-3-cephem-4-carboxylate, ethyl 7-amino-3-chloro-3-cephem-4-carboxylate, ethyl 7-amino-3 -iodomethyl-3-cephem-4-carboxylate, ethyl 7-amino-3-vinyl-3-cephem-4-carboxylate, ethyl 7-amino-3-actyloxymethyl-3-cephem-4-carboxylate, ethyl 7-amino-3-(2-furalcarbonylthiomethyl)-3-cephem-4-carboxylate, ethyl 7-amino-3-[(1,2,3-thiadiazolyl-5-yl)thiomethyl]-3-cephem-4-carboxylate, ethyl 7-amino-3-[(1-methyltetrazolyl-5-yl)thiomethyl]-3-cephem-4-carboxylate, ethyl 7-amino-3-[(Z)-2-(1,2,3-thiadiazolyl-4-yl)ethenyl]-3-cephem-4-carboxylate, ethyl 7-amino-3-[(5-methyltetrazolyl-3-yl)methyl]-3-cephem-4-carboxylate, ethyl 7-amino-3-[(Z)-2(4-methylthiazolyl-5-yl)ethenyl]-3-cephem-4-carboxylate, ethyl 7-amino-3-[(1H-1,2,3-triazolyl-5-yl)thiomethylthio]-3-cephem-4-carboxylate, isopropyl 7-amino-3-cephem-4-carboxylate, isopropyl 7-amino-3-chloro-3-cephem-4-carboxylate, isopropyl 7-amino-3-iodomethyl-3-cephem-4-carboxylate, isopropyl 7-amino-3-vinyl-3-cephem-4-carboxylate, isopropyl 7-amino-3-actyloxymethyl-3-cephem-4-carboxylate, isopropyl 7-amino-3-(2-furalcarbonylthiomethyl)-3-cephem-4- carboxylate, isopropyl 7-amino-3-[(1,2,3-thiadiazolyl-5-yl) thiomethyl]-3-cephem-4-carboxylate, isopropyl 7-amino-3-[(1-methyltetrazolyl-5-yl)thiomethyl]-3-cephem-4-carboxylate, isopropyl 7-amino-3-[(Z)-2-(1,2,3-thiadiazolyl-4-yl)ethenyl]-3-cephem-4-carboxylate, isopropyl 7-amino-3-[(5-methyltetrazolyl-3-yl)methyl]-3-cephem-4-carboxylate, isopropyl 7-amino-3-[(Z)-2(4-methylthiazolyl-5-yl)ethenyl]-3-cephem-4-carboxylate, isopropyl 7-amino-3-[(1H-1,2,3-triazolyl-5-yl)thiomethyl]-3-cephem-4-carboxylate, tert-butyl 7-amino-3-cephem-4-carboxylate, tert-butyl 7-amino-3-chloro-3-cephem-4-carboxylate, tert-butyl 7-amino-3-iodomethyl-3-cephem-4-carboxylate, tert-butyl 7-amino-3-vinyl-3-cephem-4-carboxylate, tert-butyl 7-amino-3-actyloxymethyl-3-cephem-4-carboxylate, tert-butyl 7-amino-3-(2-furalcarbonylthiomethyl)-3-cephem-4-carboxylate, tert-butyl 7-amino-3-[(1,2,3-thiadiazolyl-5-yl)thiomethyl]-3-cephem-4-carboxylate, tert-butyl 7-amino-3-[(1-methyltetrazolyl-5-yl)thiomethyl]-3-cephem-4-carboxylate, tert-butyl 7-amino-3-[(Z)-2-(1,2,3-thiadiazolyl-4-yl)ethenyl]-3-cephem-4-carboxylate, tert-butyl 7-amino-3-[(5-methyltetrazolyl-3-yl)methyl]-3-cephem-4-carboxylate, tert-butyl 7-amino-3-[(Z)-2(4-methylthiazolyl-5-yl)ethenyl]-3-cephem-4-carboxylate, tert-butyl 7-amino-3-[(1H-1,2,3-triazolyl-5-yl)thiomethylthio]-3-cephem-4-carboxylate, methoxycarbonylmethyl 7-amino-3-cephem-4-carboxylate, methoxycarbonylmethyl 7-amino-3-chloro-3-cephem-4-carboxylate, methoxycarbonylmethyl 7-amino-3-iodomethyl-3-cephem-4-carboxylate, methoxycarbonylmethyl 7-amino-3-vinyl-3-cephem-4-carboxylate, methoxycarbonylmethyl 7-amino-3-actyloxymethyl-3-cephem-4-carboxylate, methoxycarbonylmethyl 7-amino-3-(2-furalcarbonylthiomethyl)-3-cephem-4-carboxylate, -methoxycarbonylmethyl 7-amino-3-[(1,2,3-thiadiazolyl-5-yl)thiomethyl]-3-cephem-4-carboxylate, methoxycarbonylmethyl 7-amino-3-[(1-methyltetrazolyl-5-yl)thiomethyl]-3-cephem-4-carboxylate, methoxycarbonylmethyl 7-amino-3-[(Z)-2-(1,2,3-thiadiazolyl-4-yl)ethenyl]-3-cephem-4-carboxylate, methoxycarbonylmethyl 7-amino-3-[(5-methyltetrazolyl-3-yl)methyl]-3-cephem-4-carboxylate, methoxycarbonylmethyl. 7-amino-3-[(Z)-2(4-methylthiazolyl-5-yl)ethenyl]-3-cephem-4-carboxylate, methoxycarbonylmethyl 7-amino-3-[(1H-1,2,3-triazolyl-5-yl)thiomethylthio]-3-cephem-4-carboxylate, diphenylmethyl 7-amino-3-cephem-4-carboxylate, diphenylmethyl 7-amino-3-chloro-3-cephem-4-carboxylate, diphenylmethyl 7-amino-3-iodomethyl-3-cephem-4-carboxylate, diphenylmethyl 7-amino-3-vinyl-3-cephem-4-carboxylate, diphenylmethyl 7-amino-3-actyloxymethyl-3-cephem-4-carboxylate, diphenylmethyl 7-amino-3-(2-furalcarbonylthiomethyl)-3-cephem-4-carboxylate, diphenylmethyl 7-amino-3-[(1,2,3-thiadiazolyl-5-yl)thiomethyl]-3-cephem-4-carboxylate, diphenylmethyl 7-amino-3-[(1-methyltetrazolyl-5-yl)thiomethyl]-3-3-cephem-4-carboxylate, diphenylmethyl 7-amino-3-[(Z)-2-(1,2,3-thiadiazolyl-4-yl)ethenyl]-3-cephem-4-carboxylate, diphenylmethyl 7-amino-3-[(5-methyltetrazole-3-yl)methyl]-3-cephem-4-carboxylate, diphenylmethyl 7-amino-3-[(z)-2(4-methylthiazolyl-5-yl)ethenyl]-3-cephem-4-carboxylate, diphenylmethyl 7-amino-3-[(1H-1,2,3-triazolyl-5-yl)thiomethylthio]-3-3-cephem-4-carboxylate, trimethylsilyl 7-amino-3-cephem-4-carboxylate, trimethylsilyl 7-amino-3-chloro-3-cephem-4-carboxylate, trimethylsilyl 7-amino-3-iodomethyl-3-cephem-4-carboxylate, trimethylsilyl 7-amino-3-vinyl-3-cephem-4-carboxylate, trimethylsilyl 7-amino-3-actyloxymethyl-3-cephem-4-carboxylate, trimethylsilyl 7-amino-3-(2-furalcarbonylthiomethyl)-3-cephem-4-carboxylate, trimethylsilyl 7-amino-3-[(1,2,3-thiadiazole-5-yl)thiomethyl]-3-cephem-4-carboxylate, trimethylsilyl 7-amino-3-[(1-methyltetrazole-5-yl)thiomethyl]-3-cephem-4-carboxylate, trimethylsilyl 7-amino-3-[(Z)-2-(1,2,3-thiadiazolyl-4-yl)ethenyl]-3-cephem-4-carboxylate, trimethylsilyl 7-amino-3-[(5-methyltetrazole-3-yl)methyl]-3-cephem-4-carboxylate, trimethylsilyl 7-amino-3-[(Z)-2(4-methylthiazolyl-5-yl)ethenyl]-3-cephem-4-carboxylate, and trimethylsilyl 7-amino-3-[(1H-1,2,3-triazolyl-5-yl)thiomethylthio]-3-cephem-4-carboxylate, These compounds can be prepared by using, as a starting material, a 7-amino-3-acetyloxymethyl-3-cephem-4-carboxylic acid that is industrially easily available, converting the third position into a predetermined substituent, and esterifying the carboxyl group.

To obtain the peptide compound as described above, further, it is desired to use an amino acid derivative of which the carboxyl group is protected as an amine compound. There can be used any amino acid derivative of which the carboxyl group is protected without limitation provided it has an amino group and a carboxyl group in the molecules and of which the carboxyl group is protected by a protection group. Generally, however, there is used a compound in which the carboxyl group of the amino acid is protected, that is easily available as a reagent or an industrial starting material.

Here, the protection group for the carboxyl group may be an alkyl group having 1 to 4 carbon atoms, such as methyl group, ethyl group, propyl group, isopropyl group or t-butyl group, an aralkyl group having 6 to 13 carbon atoms, such as benzyl group or diphenylmethyl group, or amide group, N-methylamide group or N-benzylamide group.

Concrete examples of the amino acid derivative of which the carboxyl group is protected by the above protection group and which is preferably used for obtaining peptide compounds, include α-aminobutanoic acid, α-methylalanine, alanine, N-methylalanine, β-alanine, γ-aminobutanoic acid, 5-aminopentanoic acid, 6-aminohexanoic acid, 7-aminohexanoic acid, 8-aminooctanoic acid, 11-aminoundecanoic acid, 12-aminoundecanoic acid, asparagine, aspartic acid, β-cyclohexylalanine, cyclohexylglycine, S-acetamidecysteine, S-tert-butylcysteine, S-ethylthiocysteine, S-p-methoxybenzylcysteine, S-tritylcysteine, S-p-methylbenzylhomocysteine, glutamine, N-γ-ethylglutamine, N-γ-tritylglutamine, glutamic acid, isoglutamine, glycine, N-methylglycine, histidine, π-benzyloxymethylhistidine, 1-methylhistidine, 3-methylhistidine, isoleucine, leucine, N-methylleucine, lizine, N-ε-acetyllizine, N-ε-formylleucine, N-ε-benzyloxycarbonylleucine, methionine, norleucine, norvaline, ornithine, 4-benzoylphenylalanine, phenylalanine, 4-chlorophenylalanine, 4-fluorophenylalanine, 4-benzyloxycarbonylaminophenylalanine, homophenylalanine, phenylglycine, 4-hydroxyphenylglycine, proline, homoproline, 4-hydroxyproline, o-benzylhydroxyproline, N-methylglycine, homoserine, o-benzylhomoserine, obenzylserine, serine, o-tert-butylserine, o-methylserine, threonine, o-benzylthreonine, tryptophan, tyrosine, o-tert-butyltyrosine, o-benzyltyrosine and valine.

Quite a few of the above amino acids have asymmetric carbon atoms. In the present invention, however, there can be used L-forms, D-forms and a mixture thereof without any limitation.

These compounds are usually available as reagents or industrial starting materials. When not available, however, they can be prepared by converting the amino acid into an acid chloride thereof with a thionyl chloride followed by the reaction with an alkyl alcohol compound having 1 to 4 carbon atoms, such as methanol, ethanol, propanol, isopropanol or tert-butanol, with an aralkyl alcohol compound having 7 to 13 carbon atoms, such as benzyl alcohol or diphenyl alcohol, or with an ammonia or a primary or secondary amine having 1 to 10 carbon atoms, such as methylamine, ethylamine or benzylamine.

There is no particular limitation on the amounts of the carboxylic acid compound and the amine compound used in the method of preparing amides of the present invention. However, the reaction of the carboxyl group with the amino group in the preparation method (hereinafter also referred to as "amidation reaction") is a stoichiometric reaction. In reacting the compounds each having their respective groups in a number of one in the molecules, however, it is usually desired that the amine compound is used in an amount of from 0.8 to 1.2 moles and, particularly, in an amount of from 0.9 to 1.1 moles per a mole of the carboxylic acid compound.

It is desired that the amidation reaction is carried out in a solvent.

The condensation reaction accompanied by the dehydration like the amidation reaction of the present invention is usually carried out in a dehydrated aprotic solvent. It was made obvious that when the quaternary ammonium salt represented by the above general formula (I) is used as a condensing agent, the reaction efficiently proceeds even in a protonic organic solvent or in a system in which water is also present.

That is, in the method of preparing amides of the present invention, the amidation reaction can be carried out in water, in a protonic organic solvent or in an organic solvent containing water.

When an organic solvent containing water is used as a solvent, the organic solvent containing the water by-produced by the condensation reaction is isolated from the object product after the reaction. The solvent can then be used again without treatment or through a simple dehydration treatment, as a solvent for the amidation reaction.

Any solvent that is industrially used can be used without limitation. Concrete examples of the solvent include ethers, such as water, tetrahydrofurane, 1,4-dioxane, diethyl ether and tert-butylmethyl ether; esters such as ethyl acetate, propyl acetate and butyl acetate; nitrites such as acetonitrile and propionitrile; halogenated aliphatic hydrocarbons such as methylene chloride, chloroform and carbon tetrachloride; alcohols such as methanol,ethanol, isopropanol and tert-butanol; ketones such as acetone, methyl ethyl ketone and methylisobutyl ketone; carbonates such as dimethyl carbonate; aromatic hydrocarbons such as benzene, toluene and xylene; halogenated aromatic hydrocarbons such as chlorobenzene; amides such as dimethylformamide and dimethylacetamide; and dimethyl sulfoxides.

Among these solvents, there are preferably used, from the standpoint of expecting particularly high condensation yields, ethers such as tetrahydrofurane, 1,4-dioxane, diethyl ether and tert-butylmethyl ether; esters such as ethyl acetate, propyl acetate and butyl acetate; nitrites such as acetonitrile and propionitrile; halogenated aliphatic hydrocarbons such as methylene chloride and chloroform; alcohols such as methanol, ethanol, isopropanol and tert-butanol; ketones such as acetone, methyl ethyl ketone and methylisobutyl ketone; carbonates such as dimethyl carbonate; aromatic hydrocarbons such as benzene, toluene and xylene; and water. These solvents may be used in a single kind or being mixed together.

There is no particular limitation on the concentration of the carboxylic acid compound and the amine compound in the solvent. When the concentration is too low, however, the yield of the amide compound per one time of reaction is small, which is not economical. When the concentration is too high, on the other hand, stirring is impaired. Usually, therefore, the concentration is so selected that the concentration of the formed amide compound in the solvent is from 0.1 to 80% by weight and, preferably, from 1 to 60% by weight.

Next, described below is the procedure of operation of the method of preparing amides according to the present invention.

In the method of preparing amides according to the present invention as described above, the amidation reaction may, in principle, be conducted in the same manner as the conventional method that uses a condensing agent but using the quaternary ammonium salt represented by the above-mentioned general formula (I) as a condensing agent, and there is no limitation on the procedure of operation. From the standpoint of a high reaction yield and a short reaction time, however, it is desired to conduct the reaction by mixing three kinds of reaction reagents (i.e., condensing agent, carboxylic acid compound and amine compound). In this case, the three kinds of the reaction reagents may be reacted being mixed together, and the components need not be made present in their forms in the reaction system. For instance, the carboxylic acid compound and the amine compound may be made present in the form of a salt being neutralized.

In the above method, there is no limitation on the method of mixing the above three kinds of reaction reagents. The reaction reagents may be simultaneously added to the reaction system to mix them together. Or, the reaction reagents may be successively added to the reaction system to mix them together. From the standpoint of operability and high reaction yield, however, it is desired to add the reaction reagents into the reaction solvent maintained at a predetermined temperature successively at short time intervals to mix them together. In this case, there is no particular limitation on the order of mixing the three components. Generally, however, it is important that the carboxylic acid compound and the amine compound undergo the neutralization reaction to form a salt thereof in the solvent. For this purpose, therefore, the condensing agent is usually added after the carboxylic acid compound and the amine compound have been added.

Either the carboxylic acid compound or the amine compound may be added first. When the two are mixed together, however, the neutralization reaction takes place, usually, producing the heat of neutralization. It is probable, therefore, that the reaction system is heated at a high temperature right after the two compounds are added. If the condensing agent is added thereto shortly thereafter, therefore, the amine compound may react with the condensing agent to deteriorate the yield. It is therefore desired that the condensing agent is added after the carboxylic acid compound and the amine compound are added and after the temperature of the reaction system has lowered down to a predetermined temperature. Or, it is desired that the temperature of the solvent has been lowered down to a sufficient degree prior to adding the carboxylic acid compound and the amine compound.

An optimum reaction temperature in the amidation reaction may greatly differ depending upon the kinds of the carboxylic acid compound and the amine compound that are used, and cannot be definitely defined. When the temperature is too low, however, the rate of reaction becomes small and when the temperature is too high, there takes place a side reaction such as the reaction of the amine compound with the condensing agent. It is therefore desired that the reaction temperature lies between −30 and 60° C. and, particularly, between −20 and 50° C.

The reaction time may be suitably determined depending upon the kinds of the carboxylic acid compound and the amine compound that are use. Usually, however, the reaction time of from 0.1 to 8 hours and, preferably, from 1 to 6 hours, is sufficient. Further, the amidation reaction can be conducted under any one of normal pressure condition, elevated pressure condition or reduced pressure condition.

The thus obtained amide compound can be isolated and refined by any known method without limitation. Concretely speaking, when an organic solvent that is not compatible with water is used as the reaction solvent, there can be employed a method which washes the reaction solution with an acidic aqueous solution, an alkaline aqueous solution or water after the reaction, distills the solvent off, and isolates and refines the compound by recrystallization or through the silica gel column chromatography. When an organic solvent compatible with water is used as the reaction solvent, on the other hand, the solvent is replaced by an organic solvent that is not compatible with water after the reaction, and the compound is refined by the above-mentioned method. When the water is used as the solvent, an organic solvent that is not compatible with water is added so that the amide compound is extracted by an organic phase, and the compound is refined by the above-mentioned method. Thus, the amide compound is prepared industrially advantageously. (2) Method of preparing ester compounds by reacting a carboxylic acid compound with an alcohol compound by using the quaternary ammonium salt represented by the above general formula (I) as a condensing agent (hereinafter also referred to as a method of preparing esters of the invention).

The method of preparing esters of the resent invention can be carried out in the same manner as the conventional method of using a condensing agent but using the quaternary ammonium salt represented by the above general formula (I) as a condensing agent. Here, it is desired to mix the condensing agent comprising the above quaternary ammonium salt, a carboxylic acid compound and an alcohol compound and react them together (hereinafter also referred to as esterification reaction) in the presence of a tertiary amine compound. Presence of the tertiary amine compound helps increase the rate of esterification reaction.

In this case, there is no limitation on the kind and amount of the quaternary ammonium salt represented by the above general formula (I) used as the condensing agent, and the kind and the amount may be suitably determined depending upon the reaction system. The quaternary ammonium salts represented by the above general formula (I) can all be used for the preparation method. Among them, it is desired to use them that were exemplified above as the condensing agents that can be easily synthesized and are expected to offer high condensation yields. When the amount of the condensing agent is too small, the condensation reaction is not finished. When the amount of the condensing agent is too large, the yield tends to decrease. It is therefore desired to use the condensing agent in an amount of from 0.9 to 3 moles and, particularly, from 0.95 to 2.5 moles per a mole of the carboxylic acid compound.

As the carboxylic acid compound, further, there can be used an aliphatic carboxylic acid compound, an aromatic carboxylic compound or an amino acid derivative of which the amino group is protected, which are the same as those used in the method of preparing amides of the present invention. The reaction proceeds under mild conditions and is very effective in esterifying a compound that is subject to be decomposed by heat. It is therefore desired to use an amino acid derivative of which the amino group is protected, and its concrete examples are the same as those explained concerning the method of preparing amides of the present invention.

As the alcohol compound used in the method of preparing esters of the present invention, there can be used those compounds having primary, secondary and tertiary hydroxyl groups without limitation. Concrete examples of the alcohol compound that can be preferably used include aliphatic alcohol compounds having 1 to 10 carbon atoms, such as methanol, ethanol, 1-propanol, 2-propanol, 1-butanol, 2-butanol, 2-methyl-2-propanol, 1-pentanol, 2-pentanol, 3-pentanol, 2-methyl-2-pentanol, 3-methyl-3-pentanol, cyclopropanol, cyclopentanol, cyclohexanol and cycloheptanol; and aromatic alcohol compounds having 6 to 12 carbon atoms, such as phenol, o-cresole, m-cresole, p-cresole, benzyl alcohol, 2-phenyl-1-ethanol, 1-phenyl-1-ethanol and 3-phenyl-1-propanol.

Among these alcohols, it is desired to use those which enable the esterification reaction to easily proceed, such as methanol, ethanol, 1-propanol, 1-butanol, 1-pentanol, cyclopropanol, cyclopentanol, cyclohexanol, cycloheptanol, phenol, p-cresole, benzyl alcohol, 2-phenyl-1-ethanol, and 3-phenyl-1-propanol. These alcohol compounds are all available as industrial starting materials or reagents.

There is no particular limitation on the amount of the carboxylic acid compound and the alcohol compound used in the method of preparing esters of the present invention. However, by taking into consideration the fact that the hydroxyl group of the alcohol compound stoichiometrically reacts with the carboxyl group of the carboxylic acid compound and that the alcohol compound itself serves as a solvent, there is no particular limitation on the upper limit provided a monohydric alcohol is used in a mole number equal to that of the carboxyl group of the carboxylic acid compound. However, when the amount of the alcohol compound is too great relative to the carboxylic acid compound, the yield of the ester compound per a batch becomes small, which is not economical. It is therefore desired to use the alcohol compound in such an amount that the concentration of the carboxylic acid compound in the alcohol compound is not smaller than 0.1% by weight.

The tertiary amine compound used, as required, in the method of preparing esters of the invention can be used without limitation provided it has a tertiary amino group. Concrete examples of the tertiary amine compound that can be favorably used include aliphatic tertiary amines such as N-methylmorpholine, N-ethylmorpholine, N-methylpyrolidine, N-ethylpyrolidine, N-methylpiperidine, N-ethylpiperidine, N-methylindoline, N-methylisoindoline, triethylamine, tributylamine, dimethylisopropylamine, dimethylcyclohexylamine, N,N,N',N'-tetramethylethylenediamine, N,N,N',N'-tetramethylpropanediamine, and N,N,N',N'-tetramethylbutanediamine; and aromatic tertiary amines such as pyridine, N,N-dimethylaniline, N,N-diethylaniline, N,N-dimethylbenzylamine, N,N-diethylbenzylamine, N-methylindole, N-methylisoindole, N-methylpyrrole, indolizine and N-methylcarbazole. Among them, it is desired to use, from the standpoint of easily conducting the esterification reaction, those such as N-methylmorpholine, N-ethylmorpholine, N-methylpyrrolidine, N-ethylpyrrolidine, N-methylpiperidine, N-ethylpiperidine, triethylamine, ok; tributylamine, dimethylisopropylamine, dimethylcyclohexylamine, pyridine, N,N-dimethylaniline, N,N-diethylaniline, N,N-dimethylbenzylamine, and N,N-diethylbenzylamine. These tertiary amine compounds are all available as industrial starting materials or reagents.

There is no particular limitation on the amount of the tertiary amine compound. From the standpoint of the rate of reaction and the operability for isolation from the ester compound after the reaction, however, it is desired to use the tertiary amine compound in an amount of from 0.01 to 3 moles and, particularly, from 0.05 to 2 moles per a mole of the carboxylic acid compound.

The esterification reaction in the method of preparing esters of the invention is conducted by using the alcohol compound as a solvent provided the alcohol compound has a melting point of not higher than 0° C. However, the reaction may be carried out by using any other organic solvent. In this case, a solvent that is industrially used can be used as an organic solvent without limitation. The solvents that can be used are the same as those exemplified concerning the method of preparing amides of the present invention. There can be further preferably used the solvents that are exemplified concerning the method of preparing amides of the present invention. The solvents can similarly be reused. When the solvent is used, there is no particular limitation on the concentrations of the carboxylic acid compound and the alcohol compound in the solvent. From the standpoint of the rate of reaction and the yield per a batch, however, their amounts should be so selected that the concentration of the formed ester compound in the solvent is from 0.1 to 80% by weight and, preferably, from 1 to 60% by weight.

There is no particular limitation on the procedure of operation for mixing and reacting the condensing agent comprising the quaternary ammonium salt of the invention, a carboxylic acid compound and an alcohol compound in the presence of a tertiary amine compound. For example, the components may be simultaneously added to the reaction system and mixed, or the components may be successively added to the reaction system and mixed. From the standpoint of operability and reaction yield, however, it is desired to add the components to the reaction solvent maintained at a predetermined temperature successively with short time intervals so as to be mixed together. Here, though there is no particular limitation on the order of adding the four components, it is important that the carboxylic acid compound and the tertiary amine compound undergo the neutralization reaction to form a salt in the solution. Generally, therefore, the alcohol compound and the condensing agent are added after the carboxylic acid compound and the tertiary amine compounds have been added.

Either the carboxylic acid compound or the tertiary amine compound may be added first. When the two are mixed together, however, the neutralization reaction takes place, usually, producing the heat of neutralization. Immediately after the addition of these two compounds, therefore, the reaction system may be heated. If the alcohol compound and the condensation agent are readily added, therefore, the alcohol compound reacts with the condensing agents to decrease the yield. Therefore, the condensing agent is added after the carboxylic acid compound and the tertiary amine compound have been added and after the temperature of the reaction system has been lowered down to a predetermined temperature. Or, it is desired to lower the temperature of the solvent to a sufficient degree prior to adding the carboxylic acid compound and the tertiary amine compound.

An optimum reaction temperature in the esterification reaction may greatly differ depending upon the kinds of the carboxylic acid compound and the amine compound that are used, and cannot be definitely defined. When the temperature is too low, however, the rate of reaction becomes small and when the temperature is too high, there takes place a side reaction such as the reaction of the alcohol compound with the condensing agent. It is therefore desired that the reaction temperature lies between −30 and 60° C. and, particularly, between −20 and 50° C.

The reaction time may be suitably determined depending upon the kind and the amount of the alcohol compound. Usually, however, the reaction time of from 0.1 to 40 hours and, preferably, from 1 to 24 hours, is sufficient. Further, the reaction can be conducted under any one of a normal pressure condition, an elevated pressure condition or a reduced pressure condition.

The thus obtained ester compound can be isolated and refined by any known method without limitation. Concretely speaking, when an organic solvent that is not compatible with water is used as the reaction solvent, there can be employed a method which washes the reaction solution with an acidic aqueous solution, an alkaline aqueous solution or water after the reaction, distills the solvent off, and isolates and refines the compound by recrystallization or through the silica gel column chromatography. When an organic solvent compatible with water is used as the reaction solvent, on the other hand, the solvent is replaced by an organic solvent that is not compatible with water after the reaction, and the compound is refined by the above-mentioned method. When the water is used as the solvent, an organic solvent that is not compatible with water is added so that the ester compound is extracted by an organic phase, and the compound is refined by the above-mentioned method. Thus, the ester compound is prepared industrially advantageously.

EXAMPLES

The invention will now be described by way of Working Examples to which only, however, the invention is in noway limited.

<Preparation of Condensing Agents Used in Examples 1 to 84 and Comparative Examples 1 and 2>

Among the condensing agents comprising quaternary ammonium salts used in Examples 1 to 84, those in which X in the general formula (I') or (II) is chloro anion were prepared by reacting a triazine compound having a corresponding structure represented by the formula (III) with a tertiary amine. Further, those in which X is a perchlorate anion and those in which X is a boron tetrafluoride anion were prepared by adding sodium perchlorate and sodium tetrafluoroborate to the reaction systems so as to be reacted.

The carbodiimide condensing agents used in Comparative Examples 1 and 2 were those placed in the market as reagents.

Example 1

Into a 30-ml eggplant-type flask, there were introduced 0.30 g (2 mmols) of a 3-phenylpropionic acid, 0.27 g (2.2 mmols) of a phenetylamine and 5 ml of a tetrahydrofurane, which were, then, stirred at room temperature for 10 minutes, followed by the addition of 0.61 g (2.2 mmols) of a 4-(4,6-dimethoxy-1,3,5-triazin-2-yl)-4-methylmorpholinium chloride to conduct the reaction at room temperature for 3 hours.

After the reaction, the tetrahydrofurane was distilled off, 50 ml of a diethyl ether was added thereto, and the mixture was washed with 20 ml of a saturated aqueous solution of sodium carbonate, 20 ml of 1N hydrochloric acid and 20 ml of water. The obtained organic phase was dried by using magnesium sulfate, the diethyl ether was distilled off, and the residue was isolated and refined through a silica gel column chromatography to obtain 0.46 g of an N-phenetyl-3-phenylpropionamide (yield, 91%).

Examples 2 to 25

The operation was carried out in the same manner as in Example 1 but using carboxylic acid compounds, amine compounds and solvents shown in Table 1. The results were as shown in Table 1.

TABLE 1

| Ex. No. | Carboxylic acid compound | Amine compound | Product | Solvent | Reaction time(hrs) | Yield (%) |
|---|---|---|---|---|---|---|
| 2 | 3-phenylpropionic acid | phenetylamine | N-phenetyl-3-phenylpropionic amide | methanol | 4 | 78 |
| 3 | 3-phenylpropionic acid | phenetylamine | N-phenetyl-3-phenylpropionic amide | acetonitrile | 4 | 82 |
| 4 | 3-phenylpropionic acid | phenetylamine | N-phenetyl-3-phenylpropionic amide | ethyl acetate | 4 | 80 |
| 5 | 3-phenylpropionic acid | phenetylamine | N-phenetyl-3-phenylpropionic amide | methylene chloride | 4 | 80 |
| 6 | 3-phenylpropionic acid | phenetylamine | N-phenetyl-3-phenylpropionic amide | tetrahydrofuran/water = 9/1 | 4 | 77 |
| 7 | 3-phenylpropionic acid | phenetylamine | N-phenetyl-3-phenylpropionic amide | isopropyl alcohol | 4 | 78 |
| 8 | hexanoic acid | phenetylamine | N-phenetyl-3-hexanoic amide | tetrahydrofuran | 6 | 83 |
| 9 | hexanoic acid | phenetylamine | N-phenetyl-3-hexanoic amide | methanol | 6 | 96 |
| 10 | 3-phenyl-2-propenoic acid | phenetylamine | N-phenetyl-3-phenyl-2-propenoic amide | tetrahydrofuran | 4 | 77 |
| 11 | 3-phenyl-2-propenoic acid | phenetylamine | N-phenetyl-3-phenyl-2-propenoic amide | methanol | 4 | 92 |
| 12 | propiolic acid | phenetylamine | N-phenylpropiolic amide | tetrahydrofuran | 3 | 78 |
| 13 | pivalic acid | phenetylamine | N-phenetylpivalic amide | tetrahydrofuran | 3 | 76 |
| 14 | pivalic acid | phenetylamine | N-phenetylpivalic amide | methanol | 3 | 84 |
| 15 | p-methoxybenzoic acid | phenetylamine | N-phenetyl-p-methoxybenzoic amide | tetrahydrofuran | 4 | 82 |
| 16 | p-methoxybenzoic acid | benzylamine | N-benzyl-p-methoxybenzoic amide | tetrahydrofuran | 3 | 77 |
| 17 | p-methoxybenzoic acid | benzylamine | N-benzyl-p-methoxybenzoic amide | methanol | 3 | 96 |
| 18 | p-methoxybenzoic acid | diethylamine | N-diethyl-p-methoxybenzoic amide | tetrahydrofuran | 4 | 78 |
| 19 | p-methoxybenzoic acid | diethylamine | N-diethyl-p-methoxybenzoic amide | methanol | 4 | 80 |
| 20 | p-methoxybenzoic acid | cyclohexyl-amine | N-cyclohexyl-p-methoxybenzoic amide | tetrahydrofuran | 3 | 92 |
| 21 | benzoic acid | phenetylamine | N-phenetylbenzoic amide | tetrahydrofuran | 4 | 81 |
| 22 | benzoic acid | phenetylamine | N-phenetylbenzoic amide | methanol | 4 | 79 |
| 23 | p-nitrobenzoic acid | phenetylamine | N-phenetyl-p-nitrobenzoic amide | tetrahydrofuran | 3 | 82 |
| 24 | p-nitrobenzoic acid | phenetylamine | N-phenetyl-p-nitrobenzoic amide | methanol | 3 | 80 |
| 25 | p-hydroxybenzoic acid | phenetylamine | N-phenetyl-p-hyroxybenzoic amide | methanol | 6 | 87 |

Examples 26 to 41

The operation was carried out in the same manner as in Example 1 but using the condensing agents and solvents shown in Table 2. The results were as shown in Table 2.

TABLE 2

| Ex. No. | Condensing agent | Solvent | Reaction time(hrs) | Yield (%) |
|---|---|---|---|---|
| 26 | 4-(4,6-dimethoxy-1,3,5-triazine-2-il)-4-methylmorpholinium perchlorate | tetrahydrofuran | 4 | 81 |
| 27 | 4-(4,6-dimethoxy-1,3,5-triazine-2-il)-4-methylmorpholinium perchlorate | methanol | 4 | 77 |
| 28 | 4-(4,6-dimethoxy-1,3,5-triazine-2-il)-4-methylmorpholinium tetrafluoroborate | tetrahydrofuran | 6 | 83 |
| 29 | 4-(4,6-dimethoxy-1,3,5-triazine-2-il)-4-methylmorpholinium tetrafluoroborate | methanol | 6 | 80 |
| 30 | 4-(4,6-dimethoxy-1,3,5-triazine-2-il)-4-methylmorpholinium chloride | tetrahydrofuran | 6 | 83 |
| 31 | 4-(4,6-dimethoxy-1,3,5-triazine-2-il)-4-methylmorpholinium chloride | methanol | 6 | 95 |

TABLE 2-continued

| Ex. No. | Condensing agent | Solvent | Reaction time(hrs) | Yield (%) |
|---|---|---|---|---|
| 32 | 4-(4,6-dimethoxy-1,3,5-triazine-2-il)-4-methylmorpholinium perchlorate | tetrahydrofuran | 6 | 80 |
| 33 | 4-(4,6-dimethoxy-1,3,5-triazine-2-il)-4-methylmorpholinium perchlorate | methanol | 6 | 91 |
| 34 | 4-(4,6-dimethoxy-1,3,5-triazine-2-il)-4-ethylmorpholinium chloride | tetrahydrofuran | 6 | 84 |
| 35 | 4-(4,6-dimethoxy-1,3,5-triazine-2-il)-4-ethylmorpholinium perchlorate | tetrahydrofuran | 6 | 92 |
| 36 | 4-(4,6-dimethoxy-1,3,5-triazine-2-il)-4-methylpiperidinium chloride | tetrahydrofuran | 6 | 81 |
| 37 | 4-(4,6-dimethoxy-1,3,5-triazine-2-il)-4-methylpiperidinium perchlorate | tetrahydrofuran | 6 | 80 |
| 38 | 4-(4,6-dimethoxy-1,3,5-triazine-2-il)-4-methylpyrrolidinium chloride | tetrahydrofuran | 6 | 84 |
| 39 | 4-(4,6-dimethoxy-1,3,5-triazine-2-il)-4-methylpyrrolidinium perchlorate | tetrahydrofuran | 6 | 82 |
| 40 | (4,6-dimethoxy-1,3,5-triazine-2-il)triethylammonium perchlorate | tetrahydrofuran | 6 | 76 |
| 41 | (4,6-dimethoxy-1,3,5-triazine-2-il)pyridinium perchlorate | tetrahydrofuran | 6 | 77 |

Example 42

Into a 50-ml eggplant-type flask, there were introduced 0.30 g (1 mmol) of a (Z)-2-(2-tert-butoxycarbonylaminothiazolyl-4-yl)-2-methoxyiminoacetic acid, 0.33 g (1 mmol) of a 7-amino-3-acetoxymethyl-3-cephem-4-carboxylic acid tert-butyl ester and 10 ml of a methylene chloride, which were, then, stirred at room temperature for 10 minutes, followed by the addition of 0.29 g (1.05 mmols) of a 4-(4,6-dimethoxy-1,3,5-triazin-2-yl)-4-methylmorpholinium chloride to conduct the reaction at room temperature for 3 hours.

After the reaction, the after-treatment was conducted in the same manner as in Example 1 to obtain 0.49 g of a 7-[(Z)-2-(2-tert-butoxycarbonylaminothiazolyl-4-yl)-2-methoxyiminoacetamide]-3-acetoxymethyl-3-cephem-4-carboxylic acid tert-butyl ester (yield, 80%).

Examples 43 to 48

The operation was carried out in the same manner as in Example 42 but using, as carboxylic acid compounds, 2-aminothiazolylacetic acid derivatives and solvents shown in Table 3. The results were as shown in Table 3.

TABLE 3

| Ex. No. | 2-Aminothiazoleacetic derivatives | Product | Solvent | Reaction time(hr) | Yield (%) |
|---|---|---|---|---|---|
| 43 | (Z)-2-(2-t-butoxycarbonyl-aminothiazol-4-yl)-2-methoxyliminoacetic acid | tert-butyl 7-[(Z)-2-(2-t-butoxycarbonyl-aminothiazol-4-yl)-2-methoxyiminoacetamide]-3-acetoxymethyl-3-cephem-4-carboxylate | tetrahydro-furan | 4 | 79 |
| 44 | (Z)-2-(2-aminothiazole-4-yl)-2-methoxyiminoacetic acid | tert-butyl 7-[(Z)-2-(2-aminothiazol-4-yl)-2-methoxyiminoacetamide]-3-acetoxymethyl-3-cephem-4-carboxylate | tetrahydro-furan | 4 | 87 |
| 45 | (Z)-2-(2-aminothiazole-4-yl)-2-methoxyiminoacetic acid | tert-butyl 7-[(Z)-2-(2-aminothiazol-4-yl)-2-methoxyiminoacetamide]acetoxymethyl-3-cephem-4-carboxylate | methylene chloride | 3 | 81 |
| 46 | (Z)-2-(2-aminothiazole-4-yl)-2-(1-tert-butoxy-carbonyl-1-ethoxy)-iminoacetic acid | tert-butyl 7-[(Z)-2-(2-aminothiazol-4-yl)-2-(1-tert-butoxycarbonyl-1-methylethoxy)-iminoacetamide]-3-acetoxymethyl-3-cephem-4-carboxylate | methylene chloride | 4 | 94 |
| 47 | (Z)-2-(2-aminothiazole-4-yl)-2-(1-tert-butoxy-carbonyl-1-ethoxy)-iminoacetic acid | tert-butyl 7-[(Z)-2-(2-aminothiazol-4-yl)-2-(1-tert-butoxycarbonyl-1-methylethoxy)-iminoacetamide]-3-acetoxymethyl-3-cephem-4-carboxylate | tetrahydro-furan | 5 | 95 |
| 48 | (Z)-2-(2-chloroacetyl-aminothiazol-4-yl)-2-methoxyiminoacetic acid | tert-butyl 7-[(Z)-2-(2-chloroacetylamino-thiazol-4-yl)-2-methoxyiminoacetamide]-3-acetoxymethyl-3-cephem-4-carboxylate | methylene chloride | 5 | 80 |

Examples 49 to 58

The operation was carried out in the same manner as in Example 42 but using, as a carboxylic acid compound, a (Z)-2-(2-aminothiazolyl-4-yl)-2-methoxyiminoacetic acid which is a 2-aminothiazolylacetic acid derivative, and using, as amine compounds, 7-aminocephalosporanic acid derivatives shown in Table. 4. The results were as shown in Table 4.

TABLE 4

| Ex. No. | 7-Aminocephalosporanoic derivative | Product | Yield (%) |
|---|---|---|---|
| 49 | tert-butyl 7-amino-3-cephem-4-carboxylate | tert-butyl 7-[(Z)-2-(2-aminothiazole-4-il)-2-methoxyiminoacetamide]-3-cephem-4-carboxylate | 77 |
| 50 | tert-butyl 7-amino-3-chloro-3-cephem-4-carboxylate | tert-butyl 7-[(Z)-2-(2-aminothiazole-4-il)-2-methoxyiminoacetamide]-3-chloro-3-cephem-4-carboxylate | 81 |
| 51 | tert-butyl 7-amino-3-iodomethyl-3-cephem-4-carboxylate | tert-butyl 7-[(Z)-2-(2-aminothiazole-4-il)-2-methoxyiminoacetamide]-3-iodomethyl-3-cephem-4-carboxylate | 80 |
| 52 | tert-butyl 7-amino-3-(2-furalcarbonylthiomethyl)-3-cephem-4-carboxylate | tert-butyl 7-[(Z)-2-(2-aminothiazole-4-il)-2-methoxyiminoacetamide]-3-(2-furalcarbonylthiomethyl)-3-cephem-4-carboxylate | 77 |
| 53 | tert-butyl 7-amino-3-[(1,2,3-thiadiazole-5-il)thiomethyl]-3-cephem-4-carboxylate | tert-butyl 7-[(Z)-2-(2-aminothiazole-4-il)-2-methoxyiminoacetamide)-3-[(1,2,3-thiadiazole-5-il)thiomethyl]-3-cephem-4-carboxylate | 78 |
| 54 | tert-butyl 7-amino-3-[(1-methyltetrazole-5-il)thiomethyl]-3-cephem-4-carboxylate | tert-butyl 7-[(Z)-2-(2-aminothiazole-4-il)-2-methoxyiminoacetamide]-3-[(1-methyltetrazole-5-il)thiomethyl]-3-cephem-4-carboxylate | 77 |
| 55 | tert-butyl 7-amino-3-[(Z)-2-(1,2,3-thiadiazole-4-il)ethenyl]-3-cephem-4-carboxylate | tert-butyl 7-[(Z)-2-(2-aminothiazole-4-il)-2-methoxyiminoacetamide]-3-[(Z)-2-(1,2,3-thiadiazole-4-il)ethenyl]-3-cephem-4-carboxylate | 76 |
| 56 | tert-butyl 7-amino-3-[(5-methyltetrazole-3-il)methyl]-3-cephem-4-carboxylate | tert-butyl 7-[(Z)-2-(2-aminothiazole-4-il)-2-methoxyiminoacetamide]-3-[(5-methyltetrazole-3-il)methyl]3-cephem-4-carboxylate | 78 |
| 57 | tert-butyl 7-amino-3-[(Z)-2-(4-methylthiadiazole-5-il)ethenyl]-3-cephem-4-carboxylate | tert-butyl 7-[(Z)-2-(2-aminothiazole-4-il)-2-methoxyiminoacetamide]-3-[(Z)-2-(4-methylthiadiazole-5-il)ethenyl]-3-cephem-4-carboxylate | 75 |
| 58 | tert-butyl 7-amino-3-[(1H-1,2,3-triazole-5-il)thiomethylthio]-3-cephem-4-carboxylate | tert-butyl 7-[(Z)-2-(2-aminothiazole-4-il)-2-methoxyiminoacetamide]-3-[(1H-1,2,3-triazole-5-il)thiomethylthio]-3-cephem-4-carboxylate | 79 |

Example 59

Into a 100-ml eggplant-type flask, there were introduced 0.54 g (2 mmols) of an N-tert-butoxycarbonylphenylalanine, 0.24 g (2 mmols) of a phenetylamine and 10 ml of a methylene chloride, which were, then, stirred at room temperature for 10 minutes, followed by the addition of 0.55 g (2 mmols) of a 4-(4,6-dimethoxy-1,3,5-triazin-2-yl)-4-methylmorpholinium chloride to conduct the reaction at room temperature for 3 hours.

After the reaction, 30 ml of water was added, and the extraction operation was carried out three times with 30 ml of methylene chloride. The separated methylene chloride solution was collected, dried on magnesium sulfate and was condensed. The residue was isolated and refined through the silica gel column chromatography to obtain 0.57 g of an N'-(N-tert-butoxycarbonylphenylalanyl)phenetylamine (yield, 78%).

Example 60

Into the 100-ml eggplant-type flask, there were introduced 0.54 g (2 mmols) of an N-tert-butoxycarbonylphenylalanine, 0.24 g (2 mmols) of a phenetylamine and 10 ml of a tetrahydrofuran, which were, then, stirred at room temperature for 10 minutes, followed by the addition of 0.55 g (2 mmols) of a 4-(4,6-dimethoxy-1,3,5-triazin-2-yl)-4-methylmorpholinium chloride to conduct the reaction at room temperature for 4 hours.

After the reaction, the solvent was distilled off under a reduced pressure, 30 ml of water was added, and the extraction operation was carried out three times with 30 ml of methylene chloride. The separated methylene chloride solution was collected, dried on magnesium sulfate and was condensed. The residue was isolated and refined through the silica gel column chromatography to obtain 0.64 g of an N'-(N-tert-butoxycarbonylphenylalanyl)phenetylamine (yield, 87%).

Example 61

The operation was carried out in the same manner as in Example 60 but using, as a solvent, a mixture solution of 9 ml of tetrahydrofuran and 1 ml of water. As a result, there was obtained 0.62 g of an N'-(N-tert-butoxycarbonylphenylalanyl)phenetylamine (yield, 84%).

Example 62

The operation was carried out in the same manner as in Example 58 but using, as a condensing agent, a 1-(4,6-dimethoxy-1,3,5-triazin-2-yl)-1-ethylpiperidinium chloride. As a result, there was obtained 0.57 g of an N'1-(N-tert-butoxycarbonylphenylalanyl)phenetylamine (yield, 78%).

Example 63

The operation was carried out in the same manner as in Example 58 but using, as a condensing agent, a (4,6-dimethoxy-1,3,5-triazin-2-yl)pyridinium perchlorate. As a result, there was obtained 0.60 g of an N'-(N-tert-butoxycarbonylphenylalanyl)phenetylamine (yield, 81%).

Example 64

The operation was carried out in the same manner as in Example 58 but using, as a condensing agent, 0.47 g (1 mmol) of a 1,4-bis(4,6-dimethoxy-1,3,5-triazin-2-yl)-1,4-dimethylpiperadinium dichloride. As a result, there was obtained 0.62 g of an N'-(N-tert-butoxycarbonylphenylalanyl)phenetylamine (yield, 84%).

Example 65

Into the 100-ml eggplant-type flask, there were introduced 1.33 g (5 mmols) of an N-tert-butoxycarbonylphenylalanine, 0.90 g (5 mmols) of a phenetylaminemethyl ester and 20 ml of a methylene chloride, which were, then, stirred at room temperature for 10 minutes, followed by the slow addition of 1.43 g (5 mmols) of a 4-(4,6-dimethoxy-1,3,5-triazin-2-yl)-4-methylmorpholinium chloride to conduct the reaction for 4 hours.

After the reaction, 30 ml of the methylene chloride was added, and the mixture was washed with 30 ml of water. The solution was separated, dried on magnesium sulfate, condensed and was isolated and refined through the silica gel column chromatography to obtain 1.80 g of an N-tert-butoxycarbonyl-L-phenylalanyl-L-phenylalaninemethyl ester (yield, 84%).

Example 66

The operation was carried out in the same manner as in Example 65 but using, as a condensing agent, 1.16 g (2.5 mmols) of a 1,4-bis(4,6-dimethoxy-1,3,5-triazin-2-yl)-1,4-dimethylpiperadinium dichloride. As a result, there was obtained 1.83 g of an N-tert-butoxycarbonyl-L-phenylalanyl-L-phenylalaninemethyl ester (yield, 86%).

Examples 67 to 71

The operation was carried out in the same manner as in Example 65 but under the reaction conditions shown in Table 5. The results were as shown in Table 5.

TABLE 5

| Ex. No. | Solvent | Reaction temp. (° C.) | Reaction time (hrs) | Yield (%) |
|---|---|---|---|---|
| 67 | methylene chloride | 0 | 4 | 85 |
| 68 | tetrahydrofuran | 25 | 7 | 90 |
| 69 | acetonitrile | 25 | 4 | 87 |
| 70 | ethyl acetate | 25 | 6 | 82 |
| 71 | tetrahydrofurane/water = 9/1 | 25 | 4 | 72 |

Examples 72 to 84

The operation was carried out in the same manner as in Example 65 but using, as a carboxylic acid compound, amino acids of which the amino group is protected shown in Table 6 and using, as an amine compound, amino acids of which the carboxyl group is protected shown in Table 6. The results were as shown in Table 6.

TABLE 6

| Ex. No. | Carboxylic acid compound | Amine compound | Product | Yield (%) |
|---|---|---|---|---|
| 72 | N-benzyloxycarbonyl-L-phenylalanine | L-pheylalaninemethyl ester | N-benzyloxycarbonyl-L-phenylalanyl-L-phenylalaninemethyl ester | 91 |
| 73 | N-acetyl-L-phenylalanine | L-pheylalaninemethyl ester | N-acetyl-L-phenylalanyl-L-phenylalaninemethyl ester | 88 |
| 74 | N-tert-butoxycarbonyl-D-phenylalanine | L-pheylalaninemethyl ester | N-tert-butoxycarbonyl-D-phenylalanyl-L-pheylalaninemethyl ester | 89 |
| 75 | N-tert-butoxycarbonyl-L-phenylalanine | L-phenylalaninebenzyl ester | N-tert-butoxycarbonyl-L-phenylalanyl-L-phenylalaninebenzyl ester | 93 |
| 76 | N-methoxycarbonyl-L-phenylalanine | L-phenylalanineethyl ester | N-methoxycarbonyl-L-phenylalanyl-L-phenylalanineethyl ester | 90 |
| 77 | N-tert-butoxycarbonyl-L-phenylalanine | L-phenylalanylamide | N-tert-butoxycarbonyl-L-phenylalanyl-L-phenylalanylamide | 86 |
| 78 | N-tert-butoxycarbonylglycine | glycinemethyl ester | N-tert-butoxycarbonylglycylglycine | 91 |
| 79 | N-tert-butoxycarbonyl-L-phenylalanine | L-leucinemethyl ester | N-tert-butoxycarbonyl-L-phenylalanyl-L-leucinemethyl ester | 89 |
| 80 | N-tert-butoxycarbonyl-L-phenylalanine | L-alaninemethyl ester | N-tert-butoxycarbonyl-L-phenylalanyl-L-alaninemethyl ester | 87 |
| 81 | N-tert-butoxycarbonyl-L-alanine | L-alanine tert-butyl ester | N-tert-butoxycarbonyl-L-alanyl-L-alanine-tert-butyl ester | 92 |
| 82 | N-tert-butoxycarbonyl-L-methionine | α-methylalanine methyl ester | N-tert-butoxycarbonyl-L-methionyl-α-methylalaninemethyl ester | 80 |
| 83 | N-tert-butoxycarbonyl-α-methylalanine | L-alaninemethyl ester | N-tert-butoxycarbonyl-α-Methylalanyl-L-alaninemethyl ester | 82 |
| 84 | N-tert-butoxycarbonyl-L-leucine | L-phenylalaninemethyl ester | N-tert-butoxycarbonyl-L-leucyl-L-phenylalaninemethyl ester | 88 |

Comparative Example 1

Into the 30-ml eggplant-type flask, there were introduced 0.3 g (2 mmols) of a 3-phenylpropionic acid, 0.27 g (2.2 mmols) of a phenetylamine and 5 ml of a methanol, which were, then, stirred at room temperature for 10 minutes, followed by the slow addition of 0.45 g (2.2 mmols) of a dicyclohexylcarbodiimide (manufactured by Wako Junyaku Co.) to conduct the reaction at room temperature for 3 hours.

After the reaction, methanol was distilled off, 50 ml of diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain an N-phenetyl-3-phenylpropionamide in such a small amount as 0.03 g (yield, 5%).

Comparative Example 2

The operation was carried out in the same manner as in Comparative Example 1 but using a hydrochloric acid 1-ethyl-3-(3-dimethylaminopropyl)carbodiimide (manufactured by Wako Junyaku Co.) instead of the dicyclohexylcarbodiimide. As a result, there was obtained an N-phenetyl-3-phenylpropionamide in such a small amount as 0.04 g (yield, 8%).

Example 85

Into the 30-ml eggplant-type flask, there were introduced 0.30 g (2 mmols) of a 3-phenylpropionic acid, 0.22 g (2.2 mmols) of an N-methylmorpholine and 5 ml of methanol, which were, then, stirred at room temperature for 10 minutes, followed by the slow addition of 0.61 g (2.2 mmols) of a 4-(4,6-dimethoxy-1,3,5-triazin-2-yl)-4-methylmorpholinium chloride (hereinafter abbreviated as MMCDMT) to conduct the reaction at room temperature for 4 hours.

After the reaction, methanol was distilled off, 50 ml of a diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain 0.28 g of a methyl 3-phenylpropionate (yield, 86%).

Examples 86 to 100

The operation was carried out in the same manner as in Example 85 but using carboxylic acid compounds and alcohol compounds shown in Table 1 and using MMCDMT and N-methylmorpholine in amounts as shown in Table 1. The results were as shown in Table 7.

TABLE 7

| Ex. No. | Carboxylic acid compound | Alcohol compound | Product | MMCDMT (eg) | N-Methyl-morpholine (eg) | Reaction time (hrs) | Yield (%) |
|---|---|---|---|---|---|---|---|
| 86 | 3-phenylpropionic acid | methanol | methyl 3-phenylpropionate | 1.2 | 0.1 | 5 | 85 |
| 87 | 3-phenylpropionic acid | methanol | methyl 3-phenylpropionate | 2.0 | 1.2 | 1.5 | 93 |
| 88 | 3-phenylpropionic acid | ethanol | methyl 3-phenylpropionate | 1.2 | 0.1 | 4 | 60 |
| 89 | 3-phenylpropionic acid | ethanol | methyl 3-phenylpropionate | 2.0 | 1.2 | 1.5 | 95 |
| 90 | 3-phenylpropionic acid | 1-propanol | n-propyl 3-phenylpropionate | 2.0 | 1.2 | 1.5 | 96 |
| 91 | 3-phenylpropionic acid | 2-propanol | isopropyl 3-phenylpropionate | 2.0 | 1.2 | 16 | 89 |
| 92 | hexanoic acid | methanol | methyl hexanoate | 1.1 | 1.1 | 4 | 83 |
| 93 | hexanoic acid | ethanol | ethyl hexanoate | 1.1 | 1.1 | 4 | 88 |
| 94 | 3-phenyl-2-propenoic acid | methanol | methyl 3-phenyl-2-propenoate | 2.0 | 1.2 | 2 | 99 |
| 95 | 3-phenyl-2-propenoic acid | ethanol | ethyl 3-phenyl-2-propenoate | 2.0 | 1.2 | 2 | 98 |
| 96 | p-nitrobenzoic acid | methanol | methyl p-nitrobenzoate | 1.2 | 1.2 | 2.5 | 94 |
| 97 | terephthalic acid | methanol | dimethyl terephthalate | 2.4 | 2.2 | 4 | 64 |
| 98 | isophthalic acid | methanol | dimethyl isophthalate | 2.4 | 2.2 | 3 | 66 |
| 99 | p-methoxybenzoic acid | methanol | methyl p-methoxybenzoate | 1.2 | 1.2 | 3 | 95 |
| 100 | p-methoxybenzoic acid | ethanol | ethyl p-methoxybenzoate | 1.2 | 1.2 | 3 | 92 |

Examples 101 to 116

The procedure was carried out in the same manner as in Example 85 but using the condensing agents shown in Table 8. The results were as shown in Table 8.

TABLE 8

| Ex. No. | Condensing agent | Reaction time(hrs) | Yield (%) |
|---|---|---|---|
| 101 | 4-(4,6-dimethoxy-1,3,5-triazine-2-il)-4-methylmorpholinium perchlorate | 4 | 80 |
| 102 | 4-(4,6-dimethoxy-1,3,5-triazine-2-il)-4-methylmorpholinium perchlorate | 4 | 76 |
| 103 | 4-(4,6-dimethoxy-1,3,5-triazine-2-il)-4-methylmorpholinium tetrafluoro borate | 4 | 81 |
| 104 | 4-(4,6-dimethoxy-1,3,5-triazine-2-il)-4-methylmorpholinium tetrafluoro borate | 4 | 78 |
| 105 | 4-(4,6-dimethoxy-1,3,5-triazine-2-il)-4-methylmorpholinium chloride | 4 | 81 |
| 106 | 4-(4,6-dimethoxy-1,3,5-triazine-2-il)-4-methylmorpholinium chloride | 4 | 90 |
| 107 | 4-(4,6-dimethoxy-1,3,5-triazine-2-il)-4-methylmorpholinium perchlorate | 4 | 80 |
| 108 | 4-(4,6-dimethoxy-1,3,5-triazine-2-il)-4-methylmorpholinium perchlorate | 4 | 91 |
| 109 | 4-(4,6-dimethoxy-1,3,5-triazine-2-il)-4-ethylmorpholinium chloride | 4 | 82 |
| 110 | 4-(4,6-dimethoxy-1,3,5-triazine-2-il)-4-ethylmorpholinium perchlorate | 5 | 91 |
| 111 | 4-(4,6-dimethoxy-1,3,5-triazine-2-il)-4-methylpiperidinium chloride | 5 | 81 |
| 112 | 4-(4,6-dimethoxy-1,3,5-triazine-2-il)-4-methylpiperidinium perchlorate | 5 | 79 |
| 113 | 4-(4,6-dimethoxy-1,3,5-triazine-2-il)-4-methylpyrrolidinium chloride | 5 | 82 |
| 114 | 4-(4,6-dimethoxy-1,3,5-triazine-2-il)-4-methylpyrrolidinium perchlorate | 5 | 86 |
| 115 | (4,6-dimethoxy-1,3,5-triazine-2-il)triethylammonium perchlorate | 5 | 76 |
| 116 | (4,6-dimethoxy-1,3,5-triazine-2-il)pyridinium perchlorate | 5 | 73 |

Example 117

Into the 100-ml eggplant-type flask, there were introduced 0.54 g (2 mmols) of an N-tert-butoxycarbonylphenylalanine, 0.24 g (2.4 mmols) of an N-methylmorpholine and 10 ml of methanol, which were, then, stirred at room temperature for 10 minutes, followed by the addition of 0.55 g (2 mmols) of MMCDMT to conduct the reaction at room temperature for 3 hours.

After the reaction, 30 ml of water was added, and the extraction operation was conducted three times with 30 ml of methylene chloride. The separated methylene chloride solution was collected, dried on magnesium sulfate, condensed, and the residue was isolated and refined through the silica gel column chromatography to obtain 0.53 g of an N-tert-butoxycarbonylphenylalaninemethyl ester (yield, 94%).

Example 118

The operation was carried out in the same manner as in Example 117 but using a 1-(4,6-dimethoxy-1,3,5-triazin-2-yl)-1-ethylpiperidinium chloride as a condensing agent. As a result, there was obtained 0.52 g of an N-tert-butoxycarbonylphenylalaninemethyl ester (yield, 93%).

Example 119

The operation was carried out in the same manner as in Example 117 but using a (4,6-dimethoxy-1,3,5-triazin-2-yl) pyridinium perchlorate as a condensing agent. As a result, there was obtained 0.46 g of an N-tert-butoxycarbonylphenylalaninemethyl ester (yield, 83%).

Example 120

The operation was carried out in the same manner as in Example 117 but using 0.47 g (1 mmol) of a 1,4-bis(4,6-dimethoxy-1,3,5-triazin-2-yl)-1,4-dimethylpiperadinium chloride as a condensing agent. As a result, there was obtained 0.50 g of an N-tert-butoxycarbonylphenylalaninemethyl ester (yield, 90%).

Examples 121 to 133

The procedure was carried out in the same manner as in Example 117 but using protected amino acids shown in Table 9. The results were as shown in Table 9.

Example 134

Into the 30-ml eggplant-type flask, there were introduced 0.30 g (2 mmols) of a 3-phenylpropionic acid, 0.61 g (6 mmols) of an N-methylmorpholine, 0.24 g (2.2 mmols) of a benzyl alcohol and 5 ml of a tetrahydrofuran, which were, then, stirred at room temperature for 10 minutes, followed by the addition of 1.65 g (6 mmols) of MMCDMT to conduct the reaction at room temperature for 22 hours.

After the reaction, the tetrahydrofuran was distilled off, 50 ml of a diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain 0.43 g of a benzyl 3-phenylpropionate (yield, 89%).

Examples 135 to 149

The operation was carried out in the same manner as in Example 134 but using carboxylic acid compounds, solvents and alcohol compounds shown in Table 10. The results were as shown in Table 10.

TABLE 9

| Ex. No. | Carboxylic acid compound | Product | Yield (%) |
| --- | --- | --- | --- |
| 121 | N-benzyloxycarbonyl-L-phenylalanine | N-benzyloxycarbonyl-L-phenylalaninemethyl ester | 93 |
| 122 | N-acetyl-L-phenylanlanine | N-acetyl-L-phenylalaninemethyl ether | 90 |
| 123 | N-tert-butoxycarbonyl-D-phenylalanine | N-tert-butoxycarbonyl-D-phenylalaninemethyl ester | 92 |
| 124 | N-tert-butoxycarbonyl-L-alanine | N-tert-butoxycarbonyl-L-alaninemethyl ester | 92 |
| 125 | N-methoxycarbonyl-L-phenylalanine | N-methoxycarbonyl-L-phenylalaninemethyl ester | 91 |
| 126 | N-tert-butoxycarbonyl-L-leucine | N-tert-butoxycarbonyl-L-leucinemethyl ester | 88 |
| 127 | N-tert-butoxycarbonylglycine | N-tert-butoxycarbonylglycinemethyl ester | 96 |
| 128 | N-tert-butoxycarbonylglutamic acid | methyl N-tert-butoxycarbonylglutamate | 89 |
| 129 | N-tert-butoxycarbonyl-L-proline | N-tert-butoxycarbonyl-L-prolinemethyl ester | 92 |
| 130 | N-tert-butoxycarbonyl-β-alanine | N-tert-butoxycarbonyl-β-alaninemethyl ester | 94 |
| 131 | N-tert-butoxycarbonyl-L-methionine | N-tert-butoxycarbonyl-L-methioninemethyl ester | 84 |
| 132 | N-tert-butoxycarbonyl-α-ethylalanine | N-tert-butoxycarbonyl-α-methylalaninemethyl ester | 90 |
| 133 | N-tert-butoxycarbonyl-L-phenylglycine | N-tert-butoxycarbonyl-L-phenylglycine | 96 |

TABLE 10

| Ex. No. | Carboxylic acid compound | Solvent | Alcohol compound | Product | Reaction time (hrs) | Yield (%) |
|---|---|---|---|---|---|---|
| 135 | 3-phenylpropionic acid | ethyl acetate | benzyl alcohol | benzyl 3-phenylpropionate | 22 | 88 |
| 136 | 3-phenylpropionic acid | 1,4-dioxane | benzyl alcohol | benzyl 3-phenylpropionate | 22 | 80 |
| 137 | 3-phenylpropionic acid | methylene chloride | benzyl alcohol | benzyl 3-phenylpropionate | 20 | 84 |
| 138 | 3-phenylpropionic acid | methylene chloride | phenol | phenyl 3-phenylpropionate | 16 | 92 |
| 139 | 3-phenylpropionic acid | methylene chloride | 1-hexanol | n-hexyl 3-phenylpropionate | 24 | 81 |
| 140 | hexanoic acid | tetrahydrofuran | benzyl alcohol | benzyl hexanoate | 22 | 89 |
| 141 | hexanoic acid | methylene chloride | benzyl alcohol | benzyl hexanoate | 22 | 83 |
| 142 | hexanoic acid | tetrahydrofuran | phenol | phenyl hexanoate | 22 | 86 |
| 143 | 3-phenyl-2-propenoic acid | tetrahydrofuran | benzyl alcohol | benzyl 3-phenyl-2-propenoate | 22 | 89 |
| 144 | 3-phenyl-2-propenoic acid | methylene chloride | benzyl alcohol | benzyl 3-phenyl-2-propenoate | 23 | 83 |
| 145 | p-nitrobenzoic acid | tetrahydrofuran | benzyl alcohol | benzyl p-nitrobenzoate | 18 | 86 |
| 146 | terephthalic acid | tetrahydrofuran | benzyl alcohol | benzyl terephthalate | 30 | 70 |
| 147 | isophthalic acid | tetrahydrofuran | benzyl alcohol | benzyl isophthalate | 30 | 68 |
| 148 | p-methoxybenzoic acid | tetrahydrofuran | benzyl alcohol | benzyl p-methoxybenzoate | 17 | 89 |
| 149 | p-methoxybenzoic acid | tetrahydrofuran | phenol | phenyl p-methoxybenzoate | 15 | 88 |

<Preparation of Condensing Agents>

Preparation Example 1

Into a 500-ml eggplant-type flask, there were introduced 3.51 g (0.02 mols) of a 2-chloro-4,6-dimethoxy-1,3,5-triazine and 300 ml of a tetrahydrofuran, which were, then, stirred at room temperature for 10 minutes, followed by the addition of 2.22 g (0.02 mols) of a quinuclidine to conduct the reaction at room temperature for 10 minutes. The precipitated crystals were sucked and filtered, washed with 50 ml of a tetrahydrofuran, and were dried under a reduced pressure to obtain 5.20 g of white crystals (yield, 90.7%).

Through $^1$H-NMR, IR, ESI (Electrospray Ionization)-MS and elemental analysis, the obtained white crystals exhibited the following results.

[Results of Analysis]

① $^1$H-NMR(CD$_3$OD) σ: 2.17 (m, 6H, c), 2.32 (m, 1H, d), 4.03 (t, 6H, b), 4.15 (s, 6H, a)
② IR (KBr, cm$^{-1}$): 1592, 1464, 1374, 1096
③ ESI-MS: m/z 251.3 [(M–Cl)$^+$]
④ Elemental analysis C$_{12}$H$_{19}$ClN$_4$O$_2$: Calculated: C, 50.26; H, 6.68; N, 19.54 Measured: C, 50.12; H, 6.52; N, 19.48

From the above results of analysis, it was confirmed that the obtained white crystals were those of a 1-(4,6-dimethoxy-1,3,5-triazin-2-yl)quinulidinium chloride represented by the following formula (VIII)

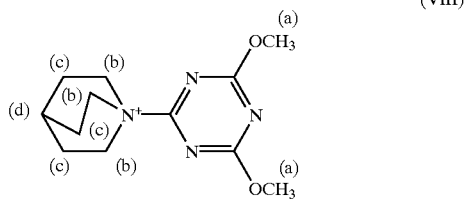

(VIII)

which was a quaternary ammonium salt of the present invention.

Preparation Example 2

The operation was carried out in the same manner as in Preparation Example 1 but using 2.54 g (0.02 mols) of a 3-quinuclidinol to obtain 5.95 g (yield, 98.3%) of white crystals of a 1-(4,6-dimethoxy-1,3,5-triazin-2-yl)-3-hydroxyquinuclidinium chloride represented by the following general formula (IX)

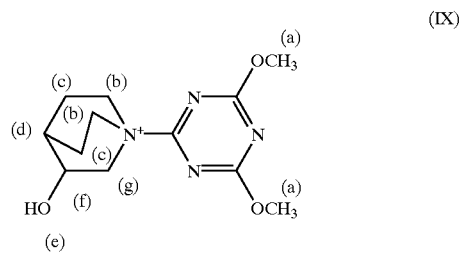

(IX)

which was a quaternary ammonium salt of the present invention. The structure of the product was confirmed by the same analysis as that of Preparation Example 1. Described below are the results of analysis.

[Results of Analysis]

① $^1$H-NMR(CD$_3$OD) σ: 2.06 (m, 2H, c), 2.23 (m, 1H, c), 2.34 (m, 1H, d), 2.47 (m, 1H, c), 3.76 (m, 1H, g), 3.90–4.04 (m, 4H, b, g), 4.15 (s, 6H, a), 4.21 (m, 1H, b), 4.37 (m, 1H, f), 4.77 (s, 1H, e)
② IR (KBr, cm$^{-1}$): 3404, 1616, 1478, 1376, 1112
③ ESI-MS: m/z 267.3 [(M–Cl)$^+$]
④ Elemental analysis C$_{12}$H$_{19}$ClN$_4$O$_3$: Calculated: C, 47.61; H, 6.33; N, 18.51 Measured: C, 47.55; H, 6.24; N, 18.48

Preparation Example 3

The operation was carried out in the same manner as in Preparation Example 1 but using 2.50 g (0.02 mols) of a 3-quinuclidinon to obtain 4.87 g (yield, 81.0%) of white crystals of a 1-(4,6-dimethoxy-1,3,5-triazin-2-yl)-3-oxoquinuclidinium chloride represented by the following general formula (X)

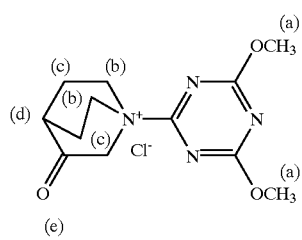

(IX)

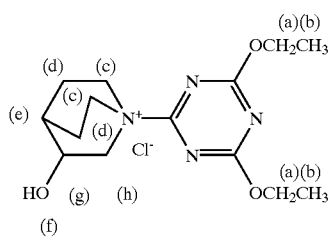

(XII)

which was a quaternary ammonium salt of the present invention. The structure of the product was confirmed by the same analysis as that of Preparation Example 1. Described below are the results of analysis.

[Results of Analysis]
① $^1$H-NMR(CD$_3$OD) σ: 2.36 (m, 2H, c), 2.52 (m, 2H, c), 2.92 (m, 1H, d), 4.11 (m, 2H, b), 4.17 (s, 6H, a), 4.36 (m, 2H, b), 4.77 (s, 2H, e)
② IR (KBr, cm$^{-1}$): 1748, 1576, 1468, 1370
③ ESI-MS: m/z 265.2 [(M−Cl)$^+$]
④ Elemental analysis C$_{12}$H$_{17}$ClN$_4$O$_3$: Calculated: C, 47.92; H, 5.70; N, 18.63 Measured: C, 47.83; H, 5.58; N, 18.50

Preparation Example 4

The operation was carried out in the same manner as in Preparation Example 1 but using 4.07 g (0.02 mols) of a 2-chloro-4,6-diethoxy-1,3,5-triazine and 2.22 g (0.02 mols) of a quinuclidine to obtain 5.73 g (yield, 91.0%) of white crystals of a 1-(4,6-diethoxy-1,3,5-triazin-2-yl) quinuclidinium chloride represented by the following general formula (XI)

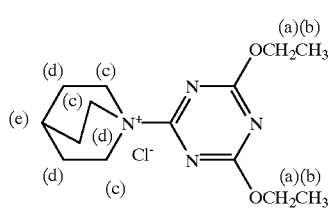

(XI)

which was a quaternary ammonium salt of the present invention. The structure of the product was confirmed by the same analysis as that of Preparation Example 1. Described below are the results of analysis.

[Results of Analysis]
① $^1$H-NMR(CD$_3$OD) σ: 1.22 (t, 6H, b), 2.18 (m, 6H, d), 2.32 (m, 1H, e), 4.04 (t, 6H, c), 4.08 (q, 4H, a)
② IR (KBr, cm$^{-1}$): 1593, 1466, 1374, 1095
③ ESI-MS: m/z 279.3 [(M−Cl)$^+$]
④ Elemental analysis C$_{14}$H$_{23}$ClN$_4$O$_2$: Calculated: C, 53.41; H, 7.36; N, 17.80 Measured: C, 53.32; H, 7.25; N, 17.73

Preparation Example 5

The operation was carried out in the same manner as in Preparation Example 1 but using 4.07 g (0.02 mols) of a 2-chloro-4,6-diethoxy-1,3,5-triazine and 2.54 g (0.02 mols) of a 3-quinuclidinol to obtain 6.51 g (yield, 98.4%) of white crystals of a 1-(4,6-diethoxy-1,3,5-triazin-2-yl)-3-hydroxyquinuclidinium chloride represented by the following general formula (XII)

which was a quaternary ammonium salt of the present invention. The structure of the product was confirmed by the same analysis as that of Preparation Example 1. Described below are the results of analysis.

[Results of Analysis]
① $^1$H-NMR(CD$_3$OD) σ: 1.23 (t, 6H, b), 2.06 (m, 2H, d), 2.22 (m, 1H, d), 2.35 (m, 1H, e), 2.47 (m, 1H, d), 3.77 (m, 1H, h), 3.89–4.04 (m, 4H, c, h), 4.08 (q, 4H, b), 4.21 (m, 1H, c), 4.37 (m, 1H, g), 4.78 (s, 1H, f)
② IR (KBr, cm$^{-1}$): 3406, 1616, 1479, 1376, 1110
③ ESI-MS: m/z 295.3 [(M−Cl)$^+$]
④ Elemental analysis C$_{14}$H$_{23}$ClN$_4$O$_3$: Calculated: C, 50.83; H, 7.01; N, 16.94 Measured: C, 50.75; H, 6.90; N, 16.79

Preparation Example 6

The operation was carried out in the same manner as in Preparation Example 1 but using 6.00 g (0.02 mols) of a 2-chloro-4,6-diphenoxy-1,3,5-triazine and 2.22 g (0.02 mols) of a quinuclidine to obtain 7.42 g (yield, 90.3%) of white crystals of a 1-(4,6-diphenoxy-1,3,5-triazin-2-yl)-3-quinuclidinium chloride represented by the following general formula (XIII)

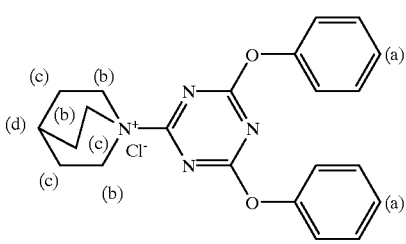

(XIII)

which was a quaternary ammonium salt of the present invention. The structure of the product was confirmed by the same analysis as that of Preparation Example 1. Described below are the results of analysis.

[Results of Analysis]
① $^1$H-NMR(CD$_3$OD) σ: 2.17 (m, 6H, c), 2.33 (m, 1H, d), 4.03 (t, 6H, b), 7.10–7.36 (m, 10H, a)
② IR (KBr, cm$^{-1}$): 1593, 1463, 1374, 1098
③ ESI-MS: m/z 375.4 [(M−Cl)$^+$]
④ Elemental analysis C$_{22}$H$_{23}$ClN$_4$O$_2$: Calculated: C, 64.31; H, 5.64; N, 13.64 Measured: C, 64.18; H, 5.51; N, 13.55

Preparation Example 7

The operation was carried out in the same manner as in Preparation Example 1 but using 6.00 g (0.02 mols) of a 2-chloro-4,6-diphenoxy-1,3,5-triazine and 2.54 g (0.02 mols) of a 3-quinuclidinol to obtain 8.38 g (yield, 98.1%) of white crystals of a 1-(4,6-diphenoxy-1,3,5-triazin-2-yl)-3- hydroxyquinuclidinium chloride represented by the following general formula (XIV)

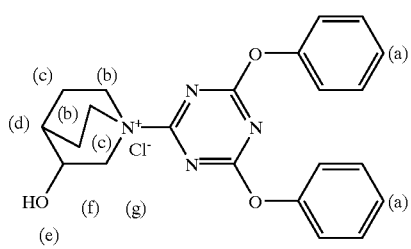

which was a quaternary ammonium salt of the present invention. The structure of the product was confirmed by the same analysis as that of Preparation Example 1. Described below are the results of analysis.

[Results of Analysis]

① $^1$H-NMR(CD$_3$OD) σ: 2.05 (m, 2H, c), 2.23 (m, 1H, c), 2.34 (m, 1H, d), 2.47 (m, 1H, c), 3.77 (m, 1H, g), 3.91–4.06 (m, 4H, b, g), 4.21 (m, 1H, b), 4.35 (m, 1H, f), 4.77 (s, 1H, e), 7.10–7.35 (m, 10H, a)

② IR (KBr, cm$^{-1}$): 3404, 1614, 1478, 1376, 1110

③ ESI-MS: m/z 391.4 [(M−Cl)$^+$]

④ Elemental analysis C$_{22}$H$_{23}$ClN$_4$O$_3$: Calculated: C, 61.90; H, 5.43; N, 13.12 Measured: C, 61.83; H, 5.31; N, 13.02

<Example 150

Into the 30-ml eggplant-type flask, there were introduced 0.30 g (2 mmols) of a 3-phenylpropionic acid, 0.27 g (2.2 mmols) of a phenetylamine as an amine compound and 5 ml of a tetrahydrofuran as a solvent, which were, then, stirred at room temperature for 10 minutes, followed by the addition of 0.67 g (2.2 mmols) of the 1-(4,6-dimethoxy-1,3,5-triazin-2-yl)-3-hydroxyquinuclidinium chloride to conduct the reaction at room temperature for 3 hours.

After the reaction, the tetrahydrofuran was distilled off, 50 ml of a diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain 0.48 g of an N-phenetyl-3-phenylpropionamide (yield, 95%).

Examples 151 to 174

The operation was carried out in the same manner as in Example 150 but using carboxylic acid compounds and amine compounds shown in Table 11. The results were as shown in Table 11.

TABLE 11

| Ex. No. | Carboxylic acid compound | Amine compound | Product | Solvent | Reaction time (hrs) | Yield (%) |
|---|---|---|---|---|---|---|
| 151 | 3-phenylpropionic acid | phenetylamine | amide N-phenetyl-3-phenylpropionate | methanol | 4 | 82 |
| 152 | 3-phenylpropionic acid | phenetylamine | amide N-phenetyl-3-phenylpropionate | acetonitrile | 4 | 88 |
| 153 | 3-phenylpropionic acid | phenetylamine | amide N-phenetyl-3-phenylpropionate | ethyl acetate | 4 | 90 |
| 154 | 3-phenylpropionic acid | phenetylamine | amide N-phenetyl-3-phenylpropionate | methylene chloride | 4 | 92 |
| 155 | 3-phenylpropionic acid | phenetylamine | amide N-phenetyl-3-phenylpropionate | tetrahydrofuran/water = 9/1 | 4 | 81 |
| 156 | 3-phenylpropionic acid | phenetylamine | amide N-phenetyl-3-phenylpropionate | isopropyl alcohol | 4 | 82 |
| 157 | hexanoic acid | phenetylamine | amide N-phenetyl-3-hexanoate | tetrahydrofuran | 6 | 88 |
| 158 | hexanoic acid | phenetylamine | amide N-phenetyl-3-hexanoate | methanol | 6 | 93 |
| 159 | 3-phenyl-2-propenoic acid | phenetylamine | amide N-phenetyl-3-phenyl-2-propenoate | tetrahydrofuran | 4 | 82 |
| 160 | 3-phenyl-2-propenoic acid | phenetylamine | amide N-phenetyl-3-phenyl-2-propenoate | methanol | 4 | 94 |
| 161 | propiolic acid | phenetylamine | amide N-phenylpropiolate | tetrahydrofuran | 3 | 84 |
| 162 | pivalic acid | phenetylamine | amide N-phenetyl pivalate | tetrahydrofuran | 3 | 83 |
| 163 | pivalic acid | phenetylamine | amide N-phenetyl pivalate | methanol | 3 | 88 |
| 164 | p-methoxybenzoic acid | phenetylamine | amide N-phenetyl-p-methoxybenzoate | tetrahydrofuran | 4 | 86 |
| 165 | p-methoxybenzoic acid | benzylamine | amide N-benzyl-p-methoxybenzoate | tetrahydrofuran | 3 | 80 |
| 166 | p-methoxybenzoic acid | benzylamine | amide N-benzyl-p-methoxybenzoate | methanol | 3 | 95 |
| 167 | p-methoxybenzoic acid | diethylamine | amide N-diethyl-p-methoxybenzoate | tetrahydrofuran | 4 | 83 |
| 166 | p-methoxybenzoic acid | diethylamine | amide N-diethyl-p-methoxybenzoate | methanol | 4 | 85 |
| 169 | p-methoxybenzoic acid | cyclohexyl-amine | amide N-cyclohexyl-p-methoxybenzoate | tetrahydrofuran | 3 | 92 |
| 170 | benzoic acid | phenetylamine | amide N-phenetylbenzoate | tetrahydrofuran | 4 | 86 |
| 171 | benzoic acid | phenetylamine | amide N-phenetylbenzoate | methanol | 4 | 82 |
| 172 | p-nitrobenzoic acid | phenetylamine | amide N-phenetyl-p-nitrobenzoate | tetrahydrofuran | 3 | 84 |

TABLE 11-continued

| Ex. No. | Carboxylic acid compound | Amine compound | Product | Solvent | Reaction time (hrs) | Yield (%) |
|---|---|---|---|---|---|---|
| 173 | p-nitrobenzoic acid | phenetylamine | amide N-phenetyl-p-nitrobenzoate | methanol | 3 | 85 |
| 174 | p-hydroxybenzoic acid | phenetylamine | amide N-phenetyl-p-hydroxybenzoate | methanol | 6 | 87 |

Examples 175 to 186

The operation was carried out in the same manner as in Example 150 but using quaternary ammonium salts (prepared in Preparation Examples 1 and 3 to 7) and solvents shown in Table 12. The results were as shown in Table 12.

TABLE 12

| Ex. No. | Condensing agent | Solvent | Reaction time (hrs) | Yield (%) |
|---|---|---|---|---|
| 175 | 1-(4,6-dimethoxy-1,3,5-triazine-2-il)quinuclidinium chloride | tetrahydrofurane | 4 | 85 |
| 176 | 1-(4,6-dimethoxy-1,3,5-triazine-2-il)quinuclidinium chloride | methanol | 4 | 83 |
| 177 | 1-(4,6-dimethoxy-1,3,5-triazine-2-il)-3-oxoquinuclidinium chloride | tetrahydrofurane | 6 | 87 |
| 178 | 1-(4,6-dimethoxy-1,3,5-triazine-2-il)-3-oxoquinuclidinium chloride | methanol | 6 | 82 |
| 179 | 1-(4,6-diethoxy-1,3,5-triazine-2-il)quinuclidinium chloride | tetrahydrofurane | 6 | 84 |
| 180 | 1-(4,6-diethoxy-1,3,5-triazine-2-il)quinuclidinium chloride | methylene chloride | 6 | 95 |
| 181 | 1-(4,6-diethoxy-1,3,5-triazine-2-il)-3-hydroxyquinuclidinium chloride | tetrahydrofurane | 6 | 84 |
| 182 | 1-(4,6-diethoxy-1,3,5-triazine-2-il)-3-hydroxyquinuclidinium chloride | methylene chloride | 6 | 91 |
| 183 | 1-(4,6-diphenoxy-1,3,5-triazine-2-il)quinuclidinium chloride | tetrahydrofurane | 6 | 85 |
| 184 | 1-(4,6-diphenoxy-1,3,5-triazine-2-il)quinuclidinium chloride | methylene chloride | 6 | 92 |
| 185 | 1-(4,6-diphenoxy-1,3,5-triazine-2-il)-3-hydroxyquinuclidinium chloride | tetrahydrofurane | 6 | 88 |
| 186 | 1-(4,6-diphenoxy-1,3,5-triazine-2-il)-3-hydroxyquinuclidinium chloride | methylene chloride | 6 | 93 |

Example 187

Into the 50-ml eggplant-type flask, there were introduced 0.30 g (1 mmol) of a (Z)-2-(2-tert-butoxycarbonylaminothiazolyl-4-yl)-2-methoxyiminoacetic acid as a carboxylic acid compound, 0.33 g (1 mmol) of a 7-amino-3-acetoxymethyl-3-cephem-4-carboxylic acid tert-butyl ester as an amine compound and 10 ml of a methylene chloride as a solvent, which were, then, stirred at room temperature for 10 minutes, followed by the addition of 0.33 g (1.1 mmols) of the same 1-(4,6-dimethoxy-1,3,5-triazin-2-yl)-3-hydroxyquinuclidinium chloride as the one prepared in the Preparation Example 2 as a condensing agent to conduct the reaction at room temperature for 3 hours.

After the reaction, the after-treatment was conducted in the same manner as in Example 150 to obtain 0.57 g of a 7-[(Z)-2-(2-tert-butoxycarbonylaminothiazolyl-4-yl)-2-methoxyiminoacetamide]-3-acetoxymethyl-3-cephem-4-carboxylic acid tert-butyl ester (yield, 93%).

Examples 188 to 193

The operation was carried out in the same manner as in Example 187 but using, as carboxylic acid compounds, 2-aminothiazole acetic derivatives and solvents shown in Table 13. The results were as shown in Table 13.

TABLE 13

| Ex. No. | 2-Aminothiazoleacetic derivatives | Products | Solvent | Reaction time (hrs) | Yield (%) |
|---|---|---|---|---|---|
| 188 | (Z)-2-(2-t-butoxycarbonyl-aminothiazole-4-il)-2-methoxyiminoacetic acid | tert-butyl 7-[(Z)-2-(2-t-butoxycarbonyl-aminothiazole-4-il)-2-methoxyiminoacetamide]-3-acetoxymethyl-3-cephem-4-carboxylate | tetra-hydrofuran | 4 | 86 |
| 189 | (Z)-2-(2-aminothiazole-4-il)-2-methoxyiminoacetic acid | tert-butyl 7-[(Z)-2-(2-aminothiazole-4-il)-2-methoxyiminoacetamide]-3-acetoxymethyl-3-cephem-4-carboxylate | tetra-chloride | 4 | 91 |
| 190 | (Z)-2-(2-aminothiazole-4-il)-2-methoxyiminoacetic acid | tert-butyl 7-[(Z)-2-(2-aminothiazole-4-il)-2-methoxyiminoacetamide]acetoxymethyl-3-cephem-4-carboxylate | methylene hydrofuran | 3 | 84 |
| 191 | (Z)-2-(2-aminothiazole-4-il)-2-(1-tert-butoxycarbonyl-1-ethoxy)-iminoacetic acid | tert-butyl 7-[(Z)-2-(2-aminothiazole-4-il)-2-(1-tert-butoxycarbonyl-1-methylethoxy)-iminoacetamide]-3-acetoxymethyl-3-cephem-4-carboxylate | methylene chloride | 4 | 93 |
| 192 | (Z)-2-(2-aminothiazole-4-il)-2-(1-tert-butoxycarbonyl-1-ethoxy)-iminoacetic acid | tert-butyl 7-[(Z)-2-(2-aminothizole-4-il)-2-(1-tert-butoxycarbonyl-1-methylethoxy)-iminoacetamide]-3-acetoxymethyl-3-cephem-4-carboxylate | tetra-hydrofuran | 5 | 95 |
| 193 | (Z)-2-(2-chloroacetyl-aminothiazole-4-il)-2-methoxyiminoacetic acid | tert-butyl 7-[(Z)-2-(2-chloroacetylamino-thiazole-4-il)-2-methoxyiminoacetamide]-3-acetoxymethyl-3-cephem-4-carboxylate | methylene chloride | 5 | 82 |

Examples 194 to 203

The operation was conducted in the same manner as in Example 187 but using a (Z)-2-(2-aminothiazolyl-4-yl)-2-methoxyiminoacetic acid which is a 2-aminothiazolylacetic acid derivative as a carboxylic acid compound and using 7-aminocephalosporanic acid derivatives shown in Table 14 as amine compounds. The results were as shown in Table 14.

After the reaction, 30 ml of water was added, and the extraction operation was conducted three times with 30 ml of methylene chloride. The separated methylene chloride solution was collected, dried on magnesium sulfate, condensed, and the residue was isolated and refined through the silica gel column chromatography to obtain 0.66 g of an N'-(N-tert-butoxycarbonyl-L-phenylalanyl)phenetylamine (yield, 90%).

TABLE 3

| Ex. No. | 2-Aminothiazoleacetic derivatives | Product | Solvent | Reaction time (hr) | Yield (%) |
|---|---|---|---|---|---|
| 43 | (Z)-2-(2-t-butoxycarbonyl-aminothiazole-4-yl)-2-methoxyiminoacetic acid | tert-butyl 7-[(Z)-2-(2-t-butoxycarbonyl-aminothiazol-4-yl)-2-methoxyiminoacetamide]-3-acetoxymethyl-3-cephem-4-carboxylate | tetrahydro-furan | 4 | 79 |
| 44 | (Z)-2-(2-aminothiazole-4-yl)-2-methoxyiminoacetic acid | tert-butyl 7-[(Z)-2-(2-aminothiazol-4-yl)-2-methoxyiminoacetamide]-3-acetoxymethyl-3-cephem-4-carboxylate | tetrahydro-furan | 4 | 87 |
| 45 | (Z)-2-(2-aminothiazole-4-yl)-2-methoxyiminoacetic acid | tert-butyl 7-[(Z)-2-(2-aminothiazol-4-yl)-2-methoxyiminoacetamide]acetoxymethyl-3-cephem-4-carboxylate | methylene chloride | 3 | 81 |
| 46 | (Z)-2-(2-aminothiazole-4-yl)-2-(1-tert-butoxy-carbonyl-1-ethoxy)-iminoacetic acid | tert-butyl 7-[(Z)-2-(2-aminothiazol-4-yl)-2-(1-tert-butoxycarbonyl-1-methylethoxy)-iminoacetamide]-3-acetoxymethyl-3-cephem-4-carboxylate | methylene chloride | 4 | 94 |
| 47 | (Z)-2-(2-aminothiazole-4-yl)-2-(1-tert-butoxy-carbonyl-1-ethoxy)-iminoacetic acid | tert-butyl 7-[(Z)-2-(2-aminothiazol-4-yl)-2-(1-tert-butoxycarbonyl-1-methylethoxy)-iminoacetamide]-3-acetoxymethyl-3-cephem-4-carboxylate | tetrahydro-furan | 5 | 95 |
| 48 | (Z)-2-(2-chloroacetyl-aminothiazol-4-yl)-2-methoxyiminoacetic acid | tert-butyl 7-[(Z)-2-(2-chloroacetylamino-thiazol-4-yl)-2-methoxyiminoacetamide]-3-acetoxymethyl-3-cephem-4-carboxylate | methylene chloride | 5 | 80 |

Example 204

Into the 100-ml eggplant-type flask, there were introduced 0.54 g (2 mmols) of an N-tert-butoxycarbonyl-L-phenylalanine as a carboxylic acid compound, 0.24 g (2.4 mmols) of a phenetylamine as an amine compound and 10 ml of a tetrahydrofuran as a solvent, which were, then, stirred at room temperature for 10 minutes, followed by the addition of 0.61 g (2 mmols) of the same 1-(4,6-dimethoxy-1,3,5-triazin-2-yl)-3-hydroxyquinuclidinium chloride as the one prepared in Preparation Example 2 as a condensing agent to conduct the reaction at room temperature for 3 hours.

Example 205

The operation was carried out in the same manner as in Example 204 but using the same 1-(4,6-dimethoxy-1,3,5-triazin-2-yl)quinuclidinium chloride as the one prepared in Preparation Example 1 as a condensing agent. As a result, there was obtained 0.65 g of an N'-(N-tert-butoxycarbonyl-L-phenylalanyl)phenetylamine (yield, 88%).

Example 206

The operation was carried out in the same manner as in Example 204 but using the same 1-(4,6-dimethoxy-1,3,5-triazin-2-yl)-3-oxoquinuclidinium chloride as the one prepared in Preparation Example 3 as a condensing agent. As a result, there was obtained 0.63 g of an N'-(N-tert-butoxycarbonyl-L-phenylalanyl)phenetylamine (yield, 85%).

there was obtained 1.88 g of an N-tert-butoxycarbonyl-L-phenylalanyl-L-phenylaminemethyl ester (yield, 88%).

Examples 209 to 221

The operation was carried out in the same manner as in Example 207 but using amino acids of which the amino group is protected shown in Table 15 as carboxylic acid compounds and using amino acids of which the carboxyl group is protected shown in Table 15 as amine compounds. The results were as shown in Table 15.

TABLE 15

| Ex. No. | Carboxylic acid compound | Amine compound | Product | Yield (%) |
|---|---|---|---|---|
| 209 | N-benzyloxycarbonyl-L-phenylalanine | L-phenylalanine-methyl ester | N-benzyloxycarbonyl-L-phenylalanyl-L-phneylalaninemethyl ester | 94 |
| 210 | N-acetyl-L-phenylalanine | L-phenylalanine-methyl ester | N-acetyl-L-phenylalanyl-L-phenylalaninemethyl ester | 90 |
| 211 | N-tert-butoxycarbonyl-D-phenylalanine | L-phenylalanine-methyl ester | N-tert-butoxycarbonyl-D-phenylalanyl-L-phenylalaninemethyl ester | 93 |
| 212 | N-tert-butoxycarbonyl-L-phenylalanine | L-phenylalanine-benzyl ester | N-tert-butoxycarbonyl-L-phenylalanyl-L-phenylalaninebenzyl ester | 94 |
| 213 | N-methoxycarbonyl-L-phenylalanine | L-phenylalanine-ethyl ester | N-methoxycarbonyl-L-phenylalanyl-L-phenylalanineethyl ester | 90 |
| 214 | N-tert-butoxycarbonyl-L-phenylalanine | L-phenylalanyl-amide | N-tert-butoxycarbonyl-L-phenylalanyl-L-phenylalanylamide | 88 |
| 215 | N-tert-butoxycarbonyl-glycine | glycinemethyl ester | N-tert-butoxycarbonylglycylglycine | 94 |
| 216 | N-tert-butoxycarbonyl-L-phenylalanine | L-leucinemethyl ester | N-tert-butoxycarbonyl-L-phenylalanyl-L-leucinemethyl ester | 90 |
| 217 | N-tert-butoxycarbonyl-L-phenylalanine | L-alaninemethyl ester | N-tert-butoxycarbonyl-L-phenylalanyl-L-alaninemethyl ester | 89 |
| 218 | N-tert-butoxycarbonyl-L-alanine | L-alanine tert-butyl ester | N-tert-butoxycarbonyl-L-alanyl-L-alanine tert-butyl ester | 92 |
| 219 | N-tert-butoxycarbonyl-L-methionine | α-methylalanine methyl | N-tert-butoxycarbonyl-L-metheonyl-α-methylalaninemethyl ester | 88 |
| 220 | N-tert-butoxycarbonyl-α-methylalanine | L-alaninemethyl ester | N-tert-butoxycarbonyl-α-methylalanyl-L-alaninemethyl ester | 85 |
| 221 | N-tert-butoxycarbonyl-L-leucine | L-phenylalanine-methyl ester | N-tert-butoxycarbonyl-L-leucine-L-phneylalaninemethyl ester | 92 |

Example 207

Into the 100-ml eggplant-type flask, there were introduced 1.33 g (5 mmols) of an N-tert-butoxycarbonyl-L-phenylalanine as a carboxylic acid compound, 0.90 g (5 mmols) of an L-phenetylaminemethyl ester as an amine compound and 20 ml of a methylene chloride as a solvent, which were, then, stirred at room temperature for 10 minutes, followed by the slow addition of 1.51 g (5 mmols) of the same 1-(4,6-dimethoxy-1,3,5-triazin-2-yl)-3-hydroxyquinuclidinium chloride as the one prepared in Preparation Example 2 as a condensing agent to conduct the reaction for 4 hours.

After the reaction, 30 ml of methylene chloride was added, and the mixture was washed with 30 ml of water, dried on magnesium sulfate, condensed, and was isolated and refined through the silica gel column chromatography to obtain 1.95 g of an N-tert-butoxycarbonyl-L-phenylalanyl-L-phenylalaninemethyl ester (yield, 91%).

Example 208

The operation was carried out in the same manner as in Example 207 but using the same 1-(4,6-dimethoxy-1,3,5-triazin-2-yl)quinuclidinium chloride as the one prepared in Preparation Example 1 as a condensing agent. As a result,

Example 222

Into the 30-ml eggplant-type flask, there were introduced 0.30 g (2 mmols) of a 3-phenylpropionic acid as a carboxylic acid compound, 0.22 g (2.2 nmols) of an N-methylmorpholine as a tertiary amine compound and 5 ml of a methanol as an alcohol compound, which were, then, stirred at room temperature for 10 minutes, followed by the addition of 0.61 g (2.2 mmols) of the same 1-(4,6-dimethoxy-1,3,5-triazin-2-yl)-3-hydroxyquinuclidinium chloride as the one prepared in Preparation Example 2 to conduct the reaction at room temperature for 4 hours.

After the reaction, the methanol was distilled off, 50 ml of a diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain 0.29 g of a methyl 3-phenylpropinate (yield, 88%).

Examples 223 to 237

The operation was carried out in the same manner as in Example 222 but using carboxylic acid compounds, alcohol compounds and condensing agents shown in Table 16, and using the N-methylmorpholine in amounts as shown in Table 16, to obtain ester compounds. The results were as shown in Table 16.

TABLE 16

| Ex. No. | Carboxylic acid compound | Alcohol compound | Product | Condensing agent (eg) | N-methyl-morpholine (eg) | Reaction time (hrs) | Yield (%) |
|---|---|---|---|---|---|---|---|
| 223 | 3-phenylpropionic acid | methanol | methyl 3-phenylpropionate | 1.2 | 0.1 | 5 | 86 |
| 224 | 3-phenylpropionic acid | methanol | methyl 3-phenylpropionate | 2.0 | 1.2 | 2 | 95 |
| 225 | 3-phenylpropionic acid | ethanol | ethyl 3-phenylpropionate | 1.2 | 0.1 | 4 | 64 |
| 226 | 3-phenylpropionic acid | ethanol | ethyl 3-phenylpropionate | 2.0 | 1.2 | 2 | 95 |
| 227 | 3-phenylpropionic acid | 1-propanol | n-propyl 3-phenylpropionate | 2.0 | 1.2 | 2 | 96 |
| 228 | 3-phenylpropionic acid | 2-propanol | isopropyl 3-phenylpropionate | 2.0 | 1.2 | 8 | 87 |
| 229 | hexanoic acid | methanol | methyl hexanoate | 1.1 | 1.1 | 4 | 89 |
| 230 | hexanoic acid | ethanol | ethyl hexanoate | 1.1 | 1.1 | 4 | 92 |
| 231 | 3-phenyl-2-propenoic acid | methanol | methyl 3-phenyl-2-propenoate | 2.0 | 1.2 | 2 | 99 |
| 232 | 3-phenyl-2-propenoic acid | ethanol | ethyl 3-phenyl-2-propenoate | 2.0 | 1.2 | 2 | 98 |
| 233 | p-nitrobenzoic acid | methanol | methyl p-nitrobenzoate | 1.2 | 1.2 | 3 | 94 |
| 234 | terephthalic acid | methanol | dimethyl terephthalate | 2.4 | 2.2 | 4 | 86 |
| 235 | isophthalic acid | methanol | dimethyl isophthalate | 2.4 | 2.2 | 3 | 80 |
| 236 | p-methoxybenzoic acid | methanol | methyl p-methoxybenzoate | 1.2 | 1.2 | 3 | 95 |
| 237 | p-methoxybenzoic acid | ethanol | ethyl p-methoxybenzoate | 1.2 | 1.2 | 3 | 93 |

Examples 238 to 243

The operation was carried out in the same manner as in Example 222 but using the condensing agents shown in Table 17 to obtain ester compounds. The results were as shown in Table 17.

TABLE 17

| Ex. No. | Condensing agent | Reaction time (hrs) | Yield (%) |
|---|---|---|---|
| 238 | 1-(4,6-dimethoxy-1,3,5-triazine-2-il)quinuclidinium chloride | 4 | 91 |
| 239 | 1-(4,6-dimethoxy-1,3,5-triazine-2-il)-3-oxoquinuclidinium chloride | 4 | 88 |
| 240 | 1-(4,6-diethoxy-1,3,5-triazine-2-il)quinuclidinium chloride | 4 | 90 |
| 241 | 1-(4,6-diethoxy-1,3,5-triazine-2-il)hydroxyquinuclidinium chloride | 4 | 88 |
| 242 | 1-(4,6-diphenoxy-1,3,5-triazine-2-il)quinuclidinium chloride | 4 | 85 |
| 243 | 1-(4,6-diphenoxy-1,3,5-triazine-2-il)-3-hydroxyquinuclidinium chloride | 4 | 83 |

Example 244

Into the 100-ml eggplant-type flask, there were introduced 0.54 g (2 mmols) of an N-tert-butoxycarbonyl-L-phenylalanine as a carboxylic acid compound, 0.24 g (2.4 mmols) of an N-methylmorpholine as a tertiary amine compound and 10 ml of methanol as an alcohol compound, which were, then, stirred at room temperature for 10 minutes, followed by the addition of 0.61 g (2 mmols) of the same 1-(4,6-dimethoxy-1,3,5-triazin-2-yl)-3-hydroxyquinuclidinium chloride as the one prepared in Preparation Example 2 as a condensing agent to conduct the reaction at room temperature for 3 hours.

After the reaction, 30 ml of water was added, and the extraction operation was conducted three times with 30 ml of methylene chloride. The separated methylene chloride solution was collected, dried on magnesium sulfate, condensed, and the residue was isolated and refined through the silica gel column chromatography to obtain 0.53 g of an N-tert-butoxycarbonyl-L-phenylalaninemethyl ester (yield, 94%).

Example 245

The operation was carried out in the same manner as in Example 244 but using the same 1-(4,6-dimethoxy-1,3,5-triazin-2-yl)quinuclidinium chloride as the one prepared in Preparation Example 1 as a condensing agent. As a result, there was obtained 0.52 g of an N-tert-butoxycarbonyl-L-phenylalaninemethyl ester (yield, 93%).

Example 246

The operation was carried out in the same manner as in Example 244 but using the same 1-(4,6-dimethoxy-1,3,5-triazin-2-yl)-3-oxoquinuclidinium chloride as the one prepared in Preparation Example 3 as a condensing agent. As a result, there was obtained 0.49 g of an N-tert-butoxycarbonyl-L-phenylalaninemethyl ester (yield, 88%).

Examples 247 to 259

The operation was carried out in the same manner as in Example 244 but using protected amino acids shown in Table 18 as carboxylic acid compounds to obtain ester compounds. The results were as shown in Table 18.

TABLE 18

| Ex. No. | Carboxylic acid compound | Product | Yield (%) |
| --- | --- | --- | --- |
| 247 | N-benzyloxycarbonyl-L-phenylalanine | N-benzyloxycarbonyl-L-phenylalaninemethyl ester | 92 |
| 248 | N-acetyl-L-phenylalanine | N-acetyl-L-phenylalaninemethyl ester | 91 |
| 249 | N-tert-butoxycarbonyl-D-phenylalanine | N-tert-butoxycarbonyl-D-phenylalaninemethyl ester | 94 |
| 250 | N-tert-butoxycarbonyl-L-alanine | N-tert-butoxycarbonyl-L-alaninemethyl ester | 93 |
| 251 | N-methoxycarbonyl-L-phenylalanine | N-methoxycarbonyl-L-phneylalaninemethyl ester | 90 |
| 252 | N-tert-butoxycarbonyl-L-leucine | N-tert-butoxycarbonyl-L-leucinemethyl ester | 88 |
| 253 | N-tert-butoxycarbonylglycine | N-tert-butoxycarbonylglycinemethyl ester | 93 |
| 254 | N-tert-butoxycarbonylglutamic acid | methyl N-tert-butoxycarbonylglutamate | 90 |
| 255 | N-tert-butoxycarbonyl-L-proline | N-tert-butoxycarbonyl-L-prolinemethyl ester | 91 |
| 256 | N-tert-butoxycarbonyl-β-alanine | N-tert-butoxycarbonyl-β-alaninemethyl ester | 94 |
| 257 | N-tert-butoxycarbonyl-L-methionine | N-tert-butoxycarbonyl-L-methioninemethyl ester | 85 |
| 258 | N-tert-butoxycarbonyl-α-Methylalanine | N-tert-butoxycarbonyl-α-methylalaninemethyl ester | 90 |
| 259 | N-tert-butoxycarbonyl-L-phenylglycine | N-tert-butoxycarbonyl-L-phenylglycine | 93 |

Example 260

Into the 30-ml eggplant-type flask, there were introduced 0.30 g (2 mmols) of a 3-phenylpropionic acid as a carboxylic acid compound, 0.61 g (6 mmols) of an N-methylmorpholine as a tertiary amine compound, 0.24 g (2.2 mmols) of a benzyl alcohol as an alcohol compound and 5 ml of a tetrahydrofuran, which were, then, stirred at room temperature for 10 minutes, followed by the addition of 1.82 g (6 mmols) of the same 1-(4,6-dimethoxy-1,3,5-triazin-2-yl)-3-hydroxyquinuclidinium chloride as the one prepared in Preparation Example 2 as a condensing agent to conduct the reaction at room temperature for 22 hours.

After the reaction, the tetrahydrofuran was distilled off, 50 ml of a diethyl ether was added, and the mixture was washed with 20 ml of a saturated aqueous solution of sodium carbonate, 20 ml of 1N hydrochloric acid and 20 ml of water. The obtained organic phase was dried on magnesium sulfate, the diethyl ether was distilled off, and the residue was isolated and refined through the silica gel column chromatography to obtain 0.43 g of a benzyl 3-phenylpropinate (yield, 90%).

Example 261

Into the 100-ml eggplant-type flask, there were introduced 2.65 g (0.01 mol) of an N-tert-butoxycarbonyl-L-phenylalanine, 1.21 g (0.01 mol) of a 2-phenylethylamine and 45 ml of an ethyl acetate (water content of 300 ppm), which were, then, stirred for 10 minutes, followed by the addition of 2.77 g (0.01 mol) of a 4-(4,6-dimethoxy-1,3,5-triazin-2-yl)-4-methylmorpholinium chloride to conduct the reaction at room temperature for 3 hours.

After the reaction, the reaction solution was washed with 30 ml of water, 30 ml of 1N hydrochloric acid and 30 ml of an 1N sodium hydroxide aqueous solution. Thereafter, ethyl acetate was distilled off under a reduced pressure, and the residue was isolated and refined through the silica gel column chromatography to obtain 3.30 g of an N'-(N-tert-butoxycarbonyl-L-phenylalanyl)-2-phenylethylamine (yield, 90%).

Next, the ethyl acetate only was isolated from the mixture solution of water and the ethyl acetate recovered in the above reaction, and new ethyl acetate was added such that the volume was 45 ml (water content of 29100 ppm) to conduct the reaction in the same manner as described above. There was obtained 3.26 g of an N'-(N-tert-butoxycarbonyl-L-phenylalanyl)-2-phenylethylamine (yield 88%).

The same operation was repeated to prepare 45 ml of ethyl acetate (water content of 29000 ppm) and to conduct the same reaction. There was obtained 3.26 g of the N'-(N-tert-butoxycarbonyl-L-phenylalanyl)-2-phenylethylamine (yield, 88%), showing no change.

Example 262

Into the 100-ml eggplant-type flask, there were introduced 2.65 g (0.01 mol) of an N-tert-butoxycarbonyl-L-phenylalanine, 1.21 g (0.01 mol) of a 2-phenylethylamine and 45 ml of a tetrahydrofuran (water content of 50 ppm), which were, then, stirred for 10 minutes, followed by the addition of 2.77 g (0.01 mol) of a 4-(4,6-dimethoxy-1,3,5-triazin-2-yl)-4-methylmorpholinium chloride to conduct the reaction at room temperature for 3 hours.

After the reaction, the tetrahydrofuran was distilled off under a reduced pressure, 45 ml of ethyl acetate was added to the residue, and the reaction solution was washed with 30 ml of water, 30 ml of 1N hydrochloric acid and 30 ml of an 1N sodium hydroxide aqueous solution. Thereafter, ethyl acetate was distilled off under a reduced pressure, and the residue was isolated and refined through the silica gel column chromatography to obtain 3.35 g of an Nl-(N-tert-butoxycarbonyl-L-phenylalanyl)-2-phenylethylamine (yield, 91%).

Next, new tetrahydrofuran was added to the tetrahydrofuran recovered in the above reaction such that the volume was 45 ml (water content of 4000 ppm) to conduct the reaction in the same manner as described above. There was obtained 3.30 g of an N'-(N-tert-butoxycarbonyl-L-phenylalanyl)-2-phenylethylamine (yield 90%).

The same operation was repeated to prepare 45 ml of ethyl acetate (water content of 7100 ppm) and to conduct the same reaction. There was obtained 3.32 g of the N'-(N-tert-butoxycarbonyl-L-phenylalanyl)-2-phenetylamine (yield, 90%).

Example 263

Into the 100-ml eggplant-type flask, there were introduced 2.65 g (0.01 mol) of an N-tert-butoxycarbonyl-L-phenylalanine, 1.01 g (0.01 mol) of an N-methylmorpholine and 45 ml of a methanol (water content of 100 ppm), which were, then, stirred for 10 minutes, followed by the addition of 2.77 g (0.01 mol) of a 4-(4,6-dimethoxy-1,3,5-triazin-2- yl)-4-methylmorpholinium chloride to conduct the reaction at room temperature for 4 hours.

After the reaction, the methanol was distilled off. To the residue was added 50 ml of a diethyl ether, and the mixture was washed with 30 ml of water, 30 ml of 1N hydrochloric acid and 30 ml of an 1N sodium hydroxide aqueous solution. Thereafter, the diethyl ether was distilled off under a reduced pressure, and the residue was isolated and refined through the silica gel column chromatography to obtain 2.60 g of an N-tert-butoxycarbonyl-L-phenylalaninemethyl ester (yield, 93%).

Next, the ethyl acetate was newly added to the methanol recovered in the above reaction such that the volume was 45 ml (water content of 29100 ppm) to conduct the reaction in the same manner as described above. There was obtained 2.59 g of an N'-(N-tert-butoxycarbonyl-L-phenylalanyl)-2-phenylethylamine (yield 93%).

The same operation was repeated to prepare 45 ml of ethyl acetate (water content of 3900 ppm) and to conduct 5 the same reaction. There was obtained 2.61 g of the N'-(N-tert-butoxycarbonyl-L-phenylalanyl)-2-phenetylamine (yield, 93%).

What is claimed is:

1. A method of preparing a carboxylic acid derivative comprising mixing a quaternary ammonium salt represented by the following general formula (I), a carboxylic acid compound and a compound having a nucleophilic functional group, to condense the carboxylic acid with the compound having the nucleophilic function group, wherein the condensation is carried out in water, in a protonic organic solvent or in an organic solvent containing water,

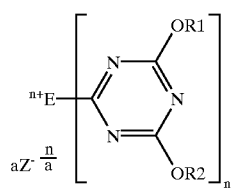

(I)

wherein
E is a monovalent or divalent organic group having one or two tertiary amino groups, said organic group being appended to the triazine ring through the nitrogen atom of said tertiary amino group;
n is 1 when E has one tertiary amino group, and is 2 when E has two tertiary amino groups,
R1 and R2 are, independently from each other, alkyl groups having 1 to 4 carbon atoms or aryl groups having 6 to 8 carbon atoms;
a is 1 or 2, and is 1 when n is 1; and
$Z^{-(n/a)}$ is a counter anion having a valency of (n/a).

2. A quaternary ammonium salt represented by the following general formula (III).

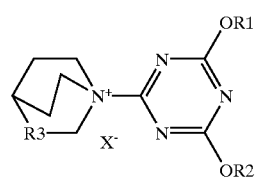

(III)

wherein R1 and R2 are, independently from each other, alkyl groups having 1 to 4 carbon atoms or aryl groups having 6 to 8 carbon atoms; and a group represented by —R3— is any one of the following groups,

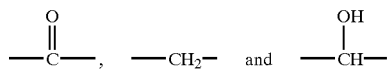

and,
X⁻ is a chloro anion, a perchlorate anion or a boron tetrafluoride anion.

3. A method of preparing a carboxylic acid derivative according to claim 1 wherein the organic solvent containing water is reused.

4. A method of preparing a carboxylic acid derivative according to claim 1 wherein the compound having a nucleophilic functional group is an amine compound and the carboxylic acid derivative is an amide compound.

5. A method of preparing a carboxylic acid derivative according to claim 4 wherein a cephem compound is prepared as an amide compound by using a 2-aminothiazolylacetic acid derivative as a carboxylic acid compound and by using a 7-aminocephalosporanic acid derivative as an amine compound.

6. A method of preparing a carboxylic acid derivative according to claim 4 wherein a peptide compound is prepared as an amide compound by using an amino acid derivative of which the amino group is protected as a carboxylic acid compound and by using an amino acid derivative of which the carboxyl group is protected as an amine compound.

7. A method of preparing a carboxylic acid derivative according to claim 1 wherein the compound having a nucleophilic functional group is an alcohol compound and the carboxylic acid derivative is an ester compound.

8. A method for preparing a carboxylic acid derivative according to claim 7 wherein an amino acid compound derivative of which the amino group is protected is used as a carboxylic acid compound.

9. A method of preparing a carboxylic acid derivative according to claim 1 wherein the quaternary ammonium salt represented by the formula (I) is at least a quaternary ammonium salt selected from quaternary ammonium salts represented by the following general formula (I') and (II),

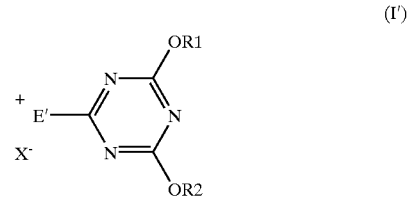

(I')

wherein
R1 and R2 are, independently from each other, alkyl groups having 1 to 4 carbon atoms or aryl groups having 6 to 8 carbon atoms;
E' is a monovalent organic group having one tertiary amino group, said organic group being appended to the triazine ring through the nitrogen atom of said tertiary amino group; and
X– is a chloro anion, a perchlorate anion, or a boron tetrafluoride anion, and

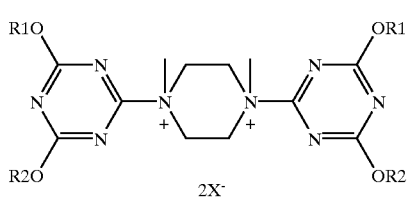

(II)

wherein R1 and R2 are, independently from each other, alkyl groups having 1 to 4 carbon atoms or aryl groups having 6 to 8 carbon atoms; and X– is a chloro anion, a perchlorate anion, or a boron tetrafluoride anion.

10. A method of preparing a carboxylic acid derivative according to claim 1 wherein the quaternary ammonium salt represented by the general formula (I) is a quaternary ammonium salt represented by the following general formula (III),

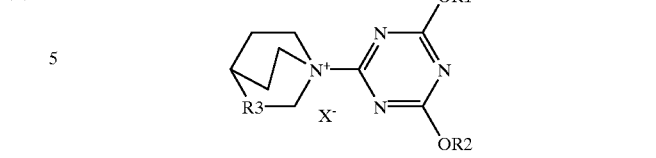

(III)

wherein
R1 and R2 are, independently from each other, alkyl groups having 1 to 4 carbon atoms or aryl groups having 6 to 8 carbon atoms; and
a group represented by —R3— is any one of the following groups,

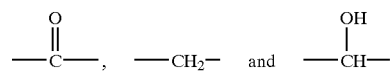

and,
X– is a chloro anion, a perchlorate anion or a boron tetrafluoride anion.

* * * * *